US012642529B2

(12) United States Patent
Sgroi, Jr. et al.

(10) Patent No.: US 12,642,529 B2
(45) Date of Patent: Jun. 2, 2026

(54) SURGICAL DEVICES INCLUDING SEALED ELECTRONIC COMPONENTS

(71) Applicant: Covidien LP, Mansfield, MA (US)

(72) Inventors: Anthony Sgroi, Jr., North Haven, CT (US); Ramiro D. Cabrera, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/871,964

(22) PCT Filed: Jun. 1, 2023

(86) PCT No.: PCT/IB2023/055641
§ 371 (c)(1),
(2) Date: Dec. 5, 2024

(87) PCT Pub. No.: WO2023/237978
PCT Pub. Date: Dec. 14, 2023

(65) Prior Publication Data

US 2025/0352213 A1     Nov. 20, 2025

Related U.S. Application Data

(60) Provisional application No. 63/350,027, filed on Jun. 8, 2022.

(51) Int. Cl.
A61B 17/064      (2006.01)
A61B 17/115      (2006.01)

(52) U.S. Cl.
CPC ................................. A61B 17/1155 (2013.01)

(58) Field of Classification Search
CPC .................................................. A61B 17/1155
See application file for complete search history.

(56) References Cited

U.S. PATENT DOCUMENTS

2018/0042610 A1 * 2/2018 Sgroi, Jr. ........... A61B 17/1155
2019/0174636 A1 * 6/2019 Sgroi, Jr .............. H05K 5/0026
(Continued)

FOREIGN PATENT DOCUMENTS

EP          3284416 A1 * 2/2018    ......... A61B 17/0684
EP          3318212 A1 * 5/2018    ............. A61B 34/76
(Continued)

OTHER PUBLICATIONS

PCT/IB2023/055641, The International Search Report and Written Opinion, mailed Aug. 18, 2023, 15pages.

*Primary Examiner* — Eyamindae C Jallow

(57)          ABSTRACT

An electronic assembly includes a first electronic component, a second electronic component, and a seal assembly. The first electronic component includes a substrate and a first electrical connecting portion secured to the substrate, and the second electronic component includes a second electrical connecting portion connected to the first electrical connecting portion forming an electronic connection between the first and second electronic components. The seal assembly includes a housing and an encapsulate. The housing defines a cavity and has one or more open sides. The housing is positioned over the electronic connection and is mated to the substrate resulting in a single open side. The encapsulate is disposed within the cavity of the housing and covers the electronic connection. The encapsulate seals closed the single open side of the housing.

19 Claims, 24 Drawing Sheets

(56) References Cited

U.S. PATENT DOCUMENTS

2020/0146166 A1 * 5/2020 Sgroi, Jr. ............. H05K 5/0247
2021/0219449 A1   7/2021 Sgori, Jr. et al.

FOREIGN PATENT DOCUMENTS

EP          3698727 A2 *  8/2020  ........... H01R 13/533
EP          3698728 A1 *  8/2020  ............. H01R 24/00
EP          3766432 A1 *  1/2021  ........... A61B 1/1155

* cited by examiner

SURGICAL DEVICES INCLUDING SEALED ELECTRONIC COMPONENTS

CROSS-REFERENCE TO RELATED APPLICATIONS

This application is a National Stage Application of PCT/IB2023/055641 filed Jun. 1, 2023, which claims benefit of and priority to U.S. Provisional Application No. 63/350,027 filed Jun. 8, 2022, and the disclosures of each of the above-identified applications are hereby incorporated by reference in their entirety.

FIELD

This disclosure generally relates to surgical devices, and more particularly, to seal assemblies for electronic components of reusable surgical devices.

BACKGROUND

Powered surgical devices include electronic components, such as printed circuit boards, switches, sensors, etc. to enhance the control of functions of the surgical devices. For example, force sensors (e.g., load reading sensors) have been used to enhance control of functions in a surgical device, such as a surgical stapling instrument. By using a force sensor, the clamping, stapling, and cutting forces of the surgical device can be monitored and used to facilitate these various functions. The force sensor can be used to detect pre-set loads and cause the surgical device to react in response thereto. For example, during clamping of thick tissue, the load will rise to a pre-determined limit where the surgical device can slow clamping to maintain the clamping force as the tissue relaxes. This allows for clamping of thick tissue without damaging the tissue (e.g., serosa tears). One such example is the firing of a circular stapler type surgical device to create an anastomosis for a powered EEA device (e.g., End-to-End Anastomosis device). The intelligence of such a surgical device is at a higher product cost compared to currently available disposable units and thus would benefit if such intelligent devices are reusable.

Reusable surgical devices must be cleaned (e.g., disinfected) using high pH solutions and sterilized prior to subsequent uses. The most common method of sterilization is the use of autoclaving. Autoclaving utilizes high pressure superheated steam (e.g., 37 PSI @137° C. for 18 minutes). Such an environment is known to damage electronic components. For example, surgical devices may suffer from moisture ingress during cleaning and/or sterilizing procedures which, in turn, may corrode and/or degrade the electronic components.

It would be beneficial if the durability of the electronic components of reusable surgical devices is enhanced to withstand cleaning and sterilization procedures (e.g., the electronic components are protected from high temperatures, steam, and/or moisture), thereby improving the reliability of the electronic components and/or extending the effective cycle life of the surgical device.

SUMMARY

Electronic assemblies of this disclosure are sealed to withstand environmental stresses associated with high pH cleaning and sterilization (e.g., autowashing and/or autoclaving), minimizing or eliminating the ingress of fluids during such processes and/or increasing the moisture resistance of the electronic assemblies thereby rendering the electronic assemblies more durable for re-use. Seal assemblies of this disclosure provide a low cost, robust, and easy to manufacture method of protecting electronic components and electronic connections between electronic components in wet or harsh environments.

In aspects, seal assemblies of the disclosure include an encapsulate and a housing. The encapsulate is used to cover and protect electronic components (e.g., a force sensor, a flex cable, etc.) and electronic connections (e.g., solder connections) between the electronic components. The encapsulate prevents contact of the electronic components and the electronic connections to wet or harsh environments in which the electronic components may corrode or degrade, or various traces can become short circuited due to the conduction of water, bodily fluids, saline, etc. The encapsulate must also withstand the harsh environments associated with cleaning and sterilization as the encapsulate may break down by repeated or prolonged contact with the harsh environments. Accordingly, the housing of the seal assemblies cover a majority of the encapsulate that would be exposed to the harsh environments thereby reducing the exposed surface area of the encapsulate to the harsh environments.

In one aspect of this disclosure, an electronic assembly includes a first electronic component, a second electronic component, and a seal assembly. The first electronic component includes a substrate and a first electrical connecting portion secured to the substrate, and the second electronic component includes a second electrical connecting portion connected to the first electrical connecting portion forming an electronic connection between the first and second electronic components. The seal assembly includes a housing and an encapsulate. The housing defines a cavity and has one or more open sides. The housing is positioned over the electronic connection and is mated to the substrate resulting in a single open side. The encapsulate is disposed within the cavity of the housing and covers the electronic connection. The encapsulate seals closed the single open side of the housing.

The first electronic component may be a sensor and/or the second electronic component may be a flexible electrical cable. The electronic connection between the first and second electronic components may be a solder connection.

In some aspects, the one or more open sides of the housing of the seal assembly includes an open bottom and an open end. The housing is positioned over the electronic connection with the open bottom positioned against the substrate of the first electronic component thereby closing the open bottom.

In some aspects, the housing is force mated to the substrate to form a seal between the housing and the substrate. The housing may include a rib disposed within the cavity that forms an interference fit between the housing and the first electrical connecting portion of the first electronic component. The seal assembly may further include a gasket forming a mated seal of the housing to the substrate. The housing may further include a living hinge.

The encapsulate may be formed using a curable liquid resin. In some aspects, the encapsulate is only exposed outside of the housing at an interface of the encapsulate with the single open side of the housing. The second electronic component may extend out of the seal assembly through the encapsulate closing the single open side of the housing.

In another aspect of this disclosure, a method of sealing an electronic connection between a first electronic component and a second electronic component includes: positioning a housing of a seal assembly over an electronic connection formed between a first electrical connecting portion of a first electronic component and a second electrical connecting portion of a second electronic component, the housing defining a cavity therein and having one or more open sides, wherein positioning the housing over the electronic connection results in the housing having a single open side; and filling the single open side of the housing with an encapsulate of the seal assembly to encapsulate the electronic connection and seal close the single open side of the housing.

The method may further include soldering the first and second electrical connecting portions together to form a solder connection.

In some aspects, the one or more open sides of the housing of the seal assembly includes an open bottom, and positioning the housing over the electronic connection includes positioning the open bottom of the housing against the substrate of the first electronic component to close the open bottom. In certain aspects, the one or more open sides of the housing of the seal assembly includes an open end, and positioning the housing over the electronic connection includes facing the open end of the housing towards the electronic connection and sliding the housing onto the substrate and over the electronic connection.

The method may further include force mating the housing to the substrate to form a seal between the housing and the substrate.

The method may further include curing the encapsulate after filling the housing with the encapsulate. In some aspects, the second electronic component extends out of the seal assembly through the single open side of the housing, and filling the single open side of the housing with the encapsulate includes pouring the encapsulate around a portion of the second electronic component extending through the single open side of the housing.

In yet another aspect of this disclosure, a surgical device includes a handle assembly, an adapter assembly extending from the handle assembly, an end effector releasably secured to the adapter assembly, and an electronic assembly disposed within the adapter assembly. The electronic assembly is configured to enable communication between the handle assembly and the end effector. The electronic assembly includes a first electronic component, a second electronic component, and a seal assembly. The first electronic component includes a substrate and a first electrical connecting portion secured to the substrate, and the second electronic component includes a second electrical connecting portion connected to the first electrical connecting portion forming an electronic connection between the first and second electronic components. The seal assembly includes a housing and an encapsulate. The housing defines a cavity and has one or more open sides. The housing is positioned over the electronic connection and is mated to the substrate resulting in a single open side. The encapsulate is disposed within the cavity of the housing and covers the electronic connection. The encapsulate seals closed the single open side of the housing.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of this disclosure are described hereinbelow with reference to the drawings, which are incorporated in and constitute a part of this specification, wherein.

DETAILED DESCRIPTION

Figure 1:
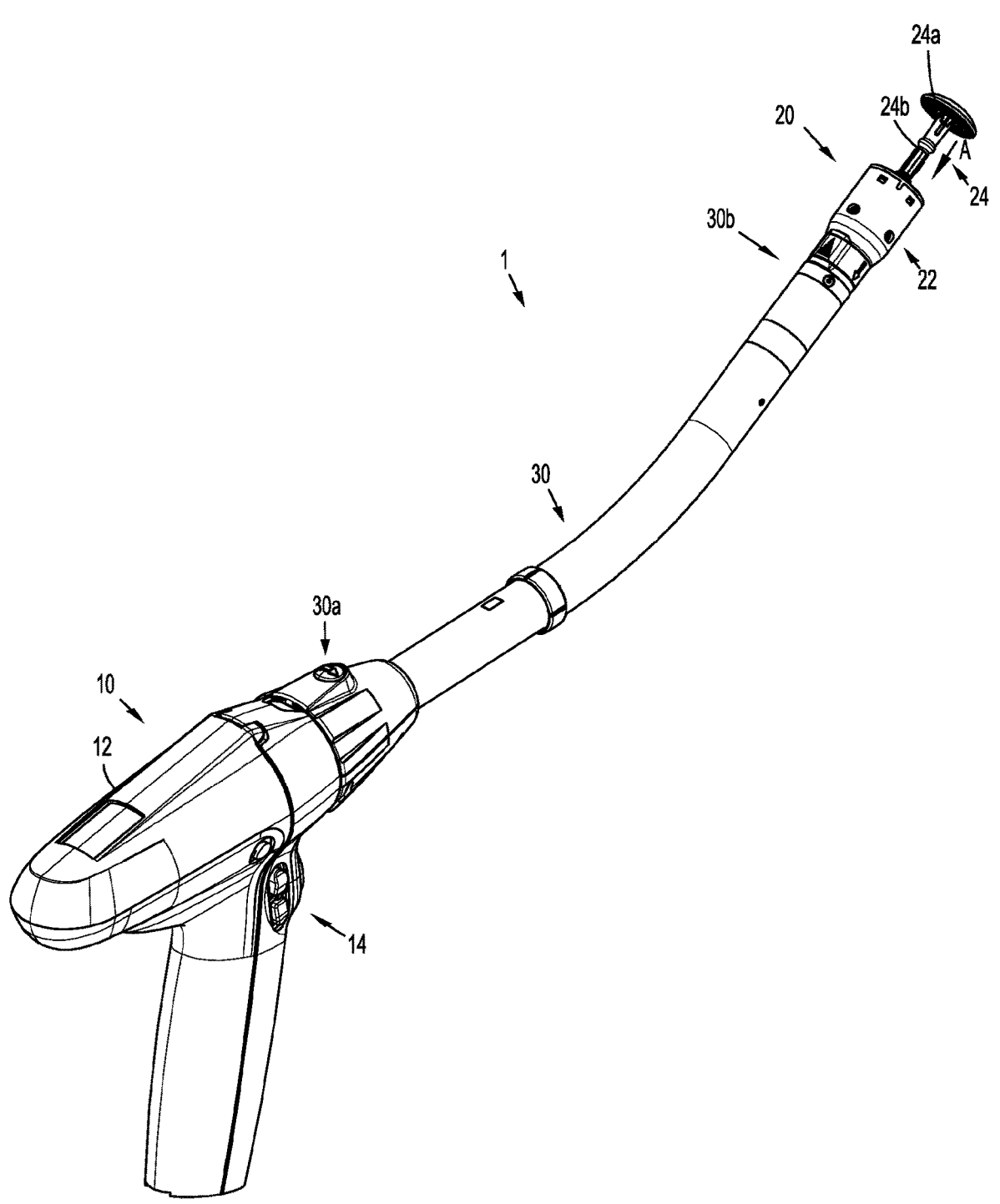
FIG. 1 is a perspective view of a surgical device in accordance with an aspect of the disclosure.

The electronic assemblies of this disclosure of, e.g., surgical devices, include electronic components and/or electronic connections between electronic components that are protected from harsh environments, such as autowashing and/or autoclaving. The electronic components and/or electronic connections are covered by a seal assembly to create a protective barrier for the electronic components and/or electronic connections, and to prevent contact of these electronic components and/or electronic connections to wet or harsh environments.

While seal assemblies of this disclosure are described with respect to sealing a force sensor and a flex cable, as well as the electronic connection between the force sensor and the flex cable, it should be understood that the seal assemblies of this disclosure are applicable for use with any electronic component(s) and/or electronic connection between electronic components in any portion of a reusable surgical or medical instrument requiring protection from wet or harsh environments.

Aspects of this disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user. Directional reference terms, such as "upper" "lower" and the like, are used to ease description of aspects of the disclosure and are not intended to have any limiting effect on the ultimate orientation of a structure or any part thereof. Additionally, it should be understood that various components of this disclosure, such as those numbered in the 100 series or plainly numbered, correspond to components of the disclosure similarly numbered in the 200, 300, 400 series or prime numbered, such that redundant explanation of similar or identical components need not be repeated herein.

Turning now to FIG. 1, a surgical device 1, in accordance with an aspect of this disclosure, is in the form of a powered handheld electromechanical instrument. The surgical device 1 includes a powered handle assembly 10, a tool assembly or end effector 20, and an adapter assembly 30 interconnecting the powered handle assembly 10 and the end effector 20. The powered handle assembly 10 is configured for selective connection with the adapter assembly 30 and, in turn, the adapter assembly 30 is configured for selective connection with the end effector 20.

The surgical device 1 will further be described to the extent necessary to disclose aspects of the disclosure. Additionally, while described and shown as including the powered handle assembly 10, the end effector 20, and the adapter assembly 30, it should be understood that a variety of surgical devices, such as those having different handle assemblies, end effectors, and/or adapter assemblies, may be utilized with aspects of the disclosure. For a detailed description of the structure and function of exemplary surgical devices, reference may be made to U.S. Pat. Nos. 10,327,779 and 10,426,468, the entire contents of each of which being incorporated herein by reference.

With continued reference to FIG. 1, the powered handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. The end effector 20 includes a loading unit 22 having a plurality of staples (not shown) disposed therein and an anvil assembly 24 including an anvil head 24*a* and an anvil rod 24*b*. The adapter assembly 30 includes a proximal portion 30*a* configured for operable connection to the handle assembly 10 and a distal portion 30*b* configured for operable connection to the end effector 20.

Figure 2:
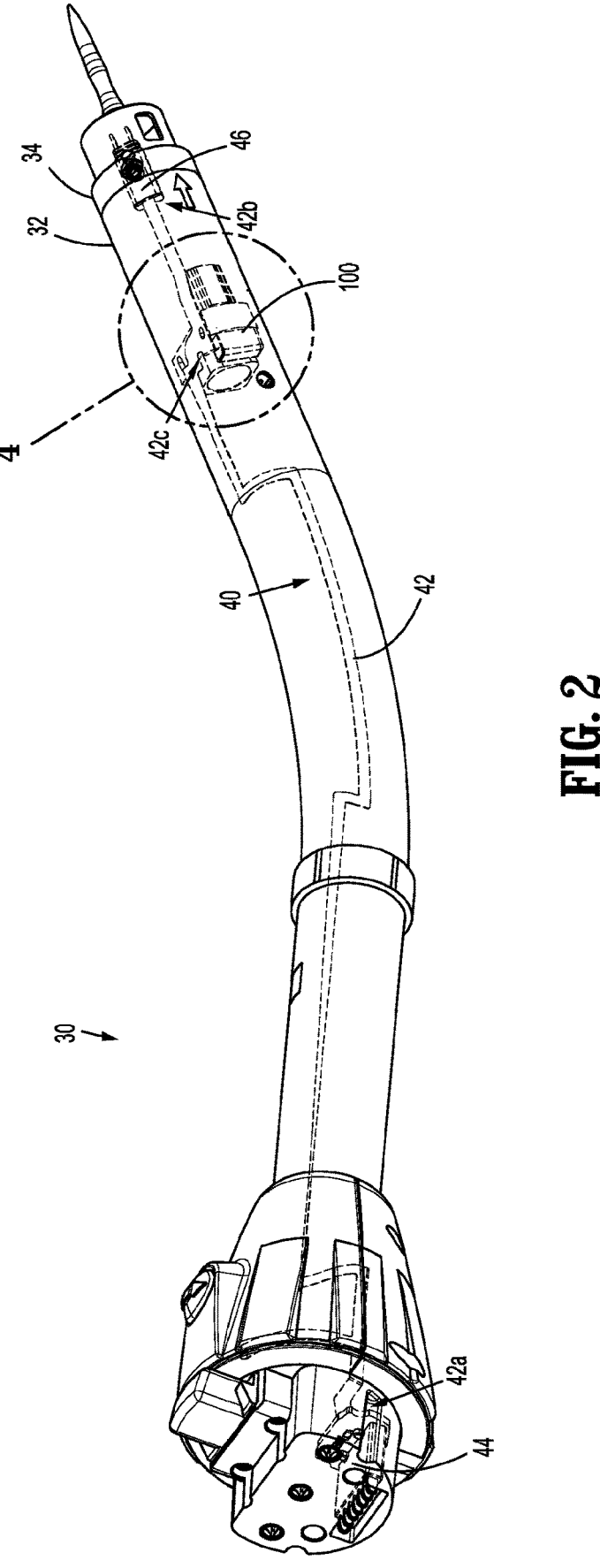
FIG. 2 is a perspective view of an adapter assembly of the surgical device of FIG. 1.

Referring now to FIG. 2, the adapter assembly 30 includes an outer sleeve 32 and a distal connector housing 34 secured to a distal end of the outer sleeve 32. The distal connector housing 34 is configured to releasably secure an end effector, e.g., the end effector 20 (FIG. 1), to the adapter assembly 30. The adapter assembly 30 includes an electronic or wiring assembly 40 (shown in phantom) disposed therein. The electronic assembly 40 is configured to enable communication between the handle assembly 10 (FIG. 1) and the end effector 20 (FIG. 1) and to relay power from the handle assembly 10 to the end effector 20. For example, this communication allows for calibration and communication of data and control signals between the end effector 20 and the adapter assembly 30, as well as between the adapter assembly 30 and the handle assembly 10, thereby transferring data pertaining to the end effector 20 to the handle assembly 10 and signals from the handle assembly 10 to the end effector 20. The electronic assembly 40 includes a force sensor 100 that detects stimuli (e.g., strain), converts the stimuli into electrical signals, and sends that data to the handle assembly 10 to affect a function of the end effector 20. It should be understood that while described and shown as a force sensor and, more specifically, as a strain gauge, other types of sensors may additionally or alternatively be utilized in the anvil assembly 30.

The electronic assembly 40 generally includes at least one flex cable 42, as well as a first electrical connector 44, a second electrical connector 46, and the force sensor 100 coupled to the flex cable 42. The flex cable 42 extends the length of the adapter assembly 30 and includes layer(s) of dielectric material isolating a series of internal traces which terminate at one or more electrical contact regions for electronic connection with the first and second electrical connectors 44, 46 and the force sensor 100. The flex cable 42 includes a first or proximal end portion 42*a* coupled to the first electrical connector 44 for electrical connection with the handle assembly 10 (FIG. 1), a second or distal end portion 42*b* coupled to the second electrical connector 46 for electrical connection with the end effector 20 (FIG. 1), and a third or intermediate end portion 42*c* electrically coupled to the force sensor 100. The dielectric layer(s) of the flex cable 42 are formed from a high performance polymer that retains its mechanical, thermal, and chemical properties when subjected to harsh environments (e.g., high temperature and/or high pressure), such as liquid crystal polymers which provide high performance in stable thin-walled applications, and the traces are formed from an electrically conductive material, such as copper.

In aspects, the flex cable 42 supports electronic components thereon (e.g., surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art). It should be understood that the flex cable 42 may be one of a plurality of cables (e.g., flex cables, adapter cables, ribbon cable, etc.) electrically coupled together to form a wiring harness or a flexible electrical cable, as is within the purview of those skilled in the art.

Figure 3A:
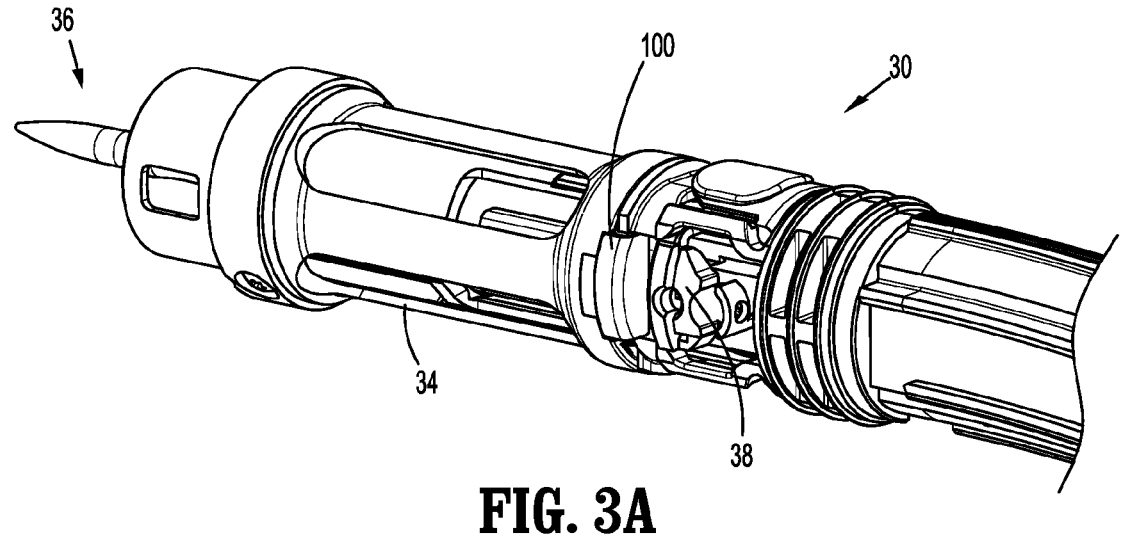
FIG. 3A is a perspective view of a distal end portion of the adapter assembly of FIGS. 1 and 2, with an outer sleeve of the adapter assembly removed therefrom.

As shown in FIG. 3A, the adapter assembly 30 further includes a trocar assembly 36 that extends through a central aperture 101 (see e.g., FIG. 4) of the force sensor 100 and a central aperture 39 (FIG. 3B) of a trocar connection housing 38. The trocar connection housing 38 releasably secures the trocar assembly 36 relative to the outer sleeve 32 (FIG. 2) of the adapter assembly 30. The force sensor 100 is disposed between the trocar connection housing 38 and the distal connector housing 34 of the adapter assembly 30, and is configured to measure forces along a load path. Specifically, the force sensor 100 measures forces of the end effector 20 (e.g., as shown in FIG. 1, the pressure applied by the anvil head 24a in the direction of arrow "A" against the distal portion 30b of the adapter assembly 30, the pressure applied by tissue acting on the anvil head 24a in a direction opposite of arrow "A" as the anvil head 24a is closed onto tissue, etc.).

Figure 3B:
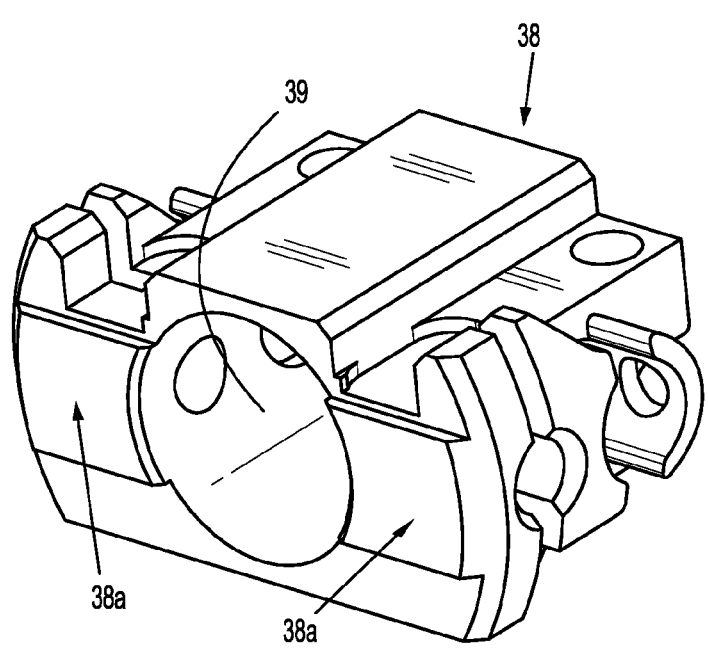
FIG. 3B is an enlarged perspective view of a trocar connection housing of the adapter assembly of FIG. 3A.
Figure 3C:
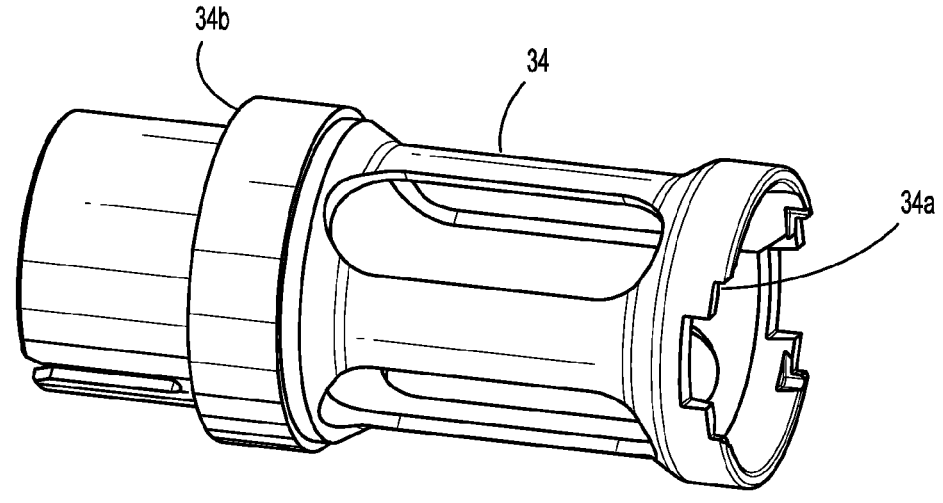
FIG. 3C is an enlarged perspective view of a connector housing of the adapter assembly of FIG. 3A.
Figure 4:
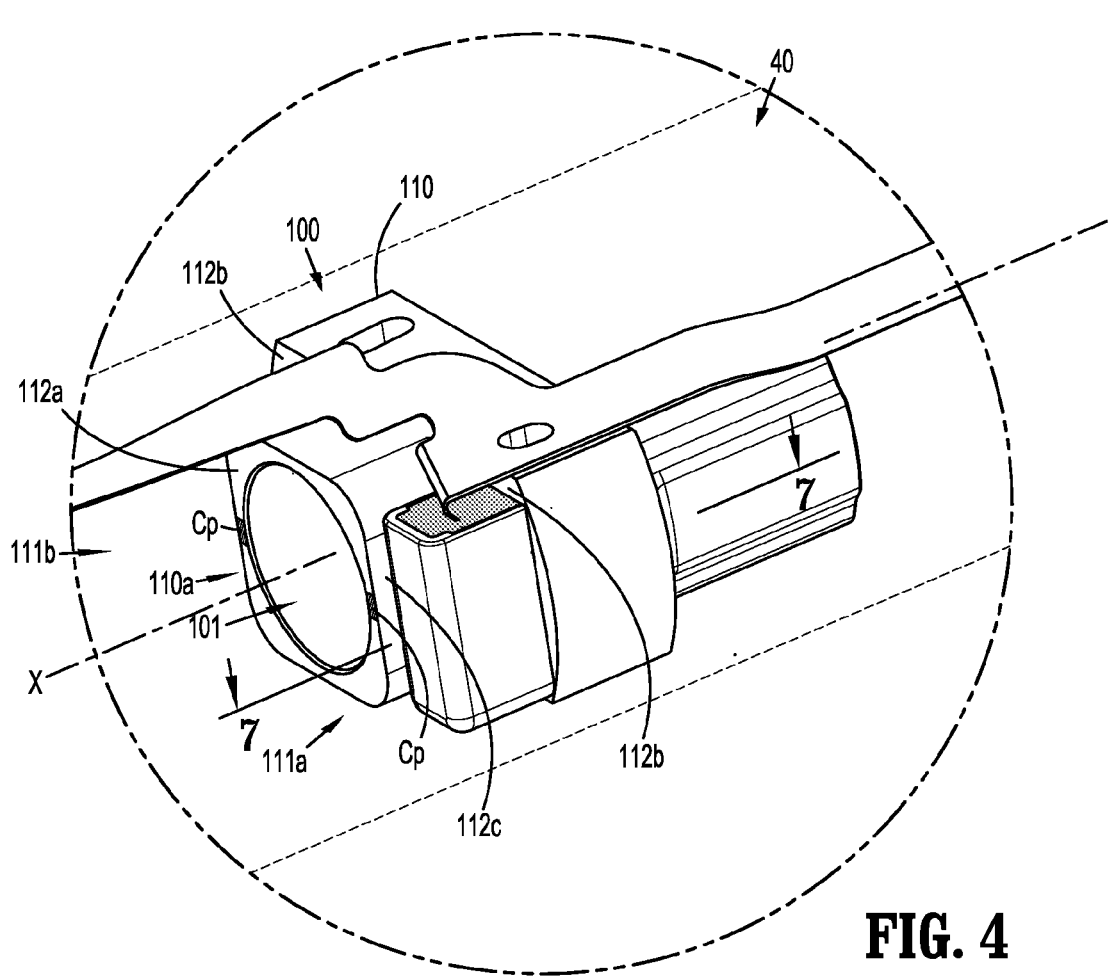
FIGS. 4 and 5 are perspective views of a portion of an electronic assembly of the adapter assembly of FIG. 2, the electronic assembly including a force sensor, a flex cable, and a seal assembly in accordance with an aspect of the disclosure.
Figure 5:
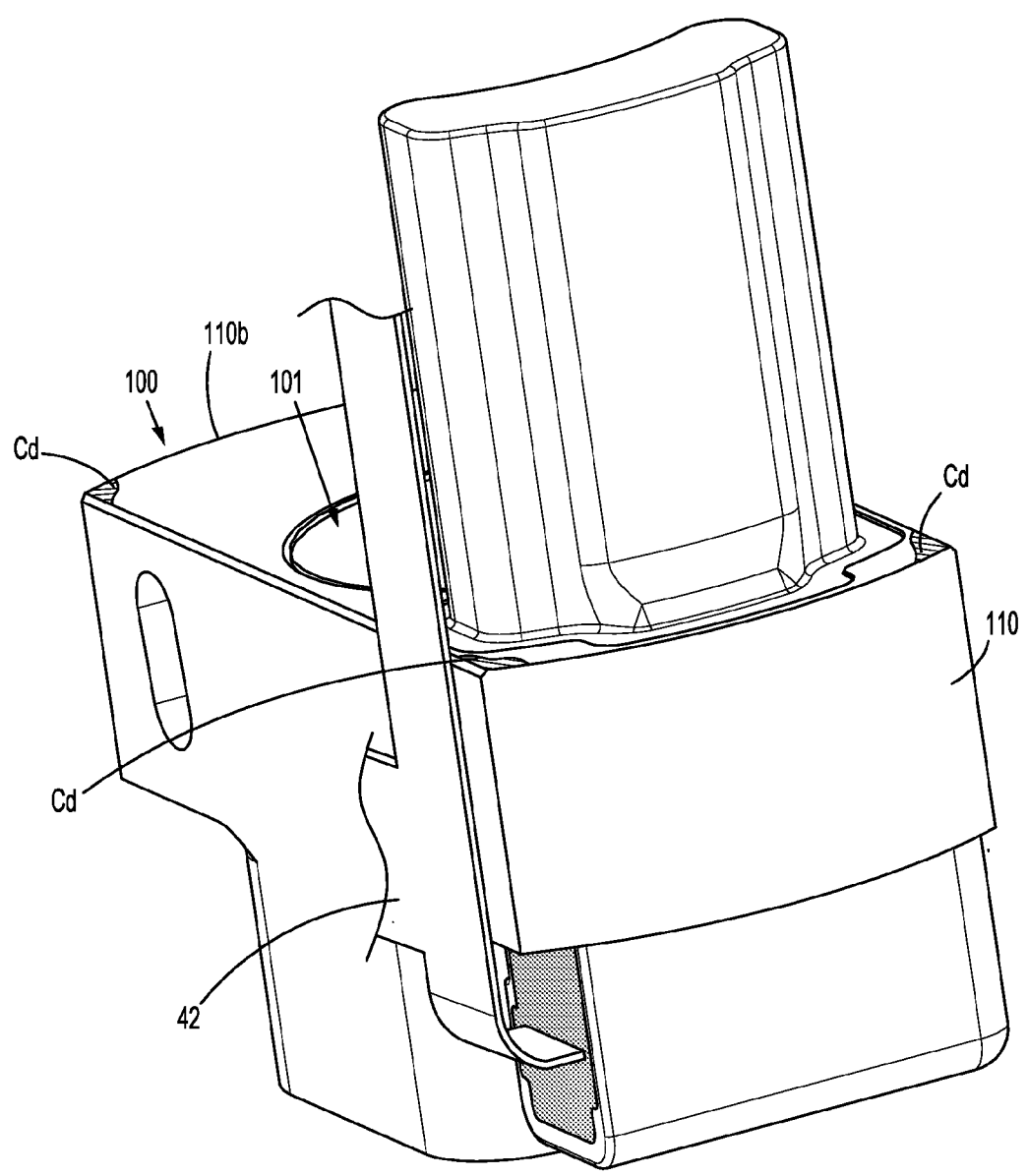

As shown in FIGS. 3B and 4, the trocar connection housing 38 includes a distal surface 38a which interfaces with and loads a proximal surface 110a of a body or substrate 110 of the force sensor 100 at proximal load contact areas "Cp". As shown in FIGS. 3C and 5, a proximal surface 34a of the distal connector housing 34 interfaces with and loads a distal surface 110b of the substrate 110 of the force sensor 100 at distal load contact areas "Cd" (e.g., disposed in each of the corners of the distal surface 110b). Thus, for example, as the anvil assembly 24 (FIG. 1) is approximated towards the loading unit 22 (FIG. 1) of the end effector 20 (FIG. 1) during clamping and/or stapling of tissue, the anvil head 24a applies uniform pressure in the direction of arrow "A" (FIG. 1) against the distal end 34b of the distal connector housing 34 which, in turn, is transmitted to the distal load contact areas "Cd" of the force sensor 100.

As shown in FIGS. 4 and 5, the substrate 110 of the force sensor 100 has a central aperture 101 defined through the proximal and distal surfaces 110a, 110b and extending along a central longitudinal axis "X" of the substrate 110. The substrate 110 is divided into first and second lateral halves 111a. 111b by a plane passing through the central longitudinal axis "X". The proximal surface 110a (FIG. 4) and the distal surface 110b (FIG. 5) of the substrate 110 are load bearing surfaces having proximal and distal load contact areas "Cp." "Cd." respectively, as described above, that allow the substrate 110 to compress when loaded by the surgical device 1 (FIG. 1). The substrate 110 is formed from a rigid material having high strength and high temperature endurance, such as a metal (e.g., stainless steel).

As seen in FIG. 4, the proximal surface 110a of substrate 110 is a stepped surface including a central wall 112a, lateral walls 112b, and intermediate walls 112c interconnecting the central and lateral walls 112a, 112b. The central wall 112a is substantially planar and extends along a plane lying substantially perpendicular to the central longitudinal axis "X" of the substrate 110, and the lateral walls 112b are also planar and extend along a plane lying substantially perpendicular to the central longitudinal axis "X" of the substrate 110 in longitudinally spaced and distal relation relative to the central wall 112a. The intermediate walls 112c are substantially planar and extend along a plane lying substantially parallel to the central longitudinal axis "X" of the substrate 110. It should be understood that the proximal surface 110a may have other configurations, such as, for example, angled lateral walls. As seen in FIG. 5, the distal surface 110b of the substrate 110 is substantially planar and extends along a plane lying substantially perpendicular to the central longitudinal axis "X" (FIG. 4) of the substrate 110 and substantially parallel to the central and lateral walls 112a, 112b (FIG. 4) of the proximal surface 110a.

Figure 6:
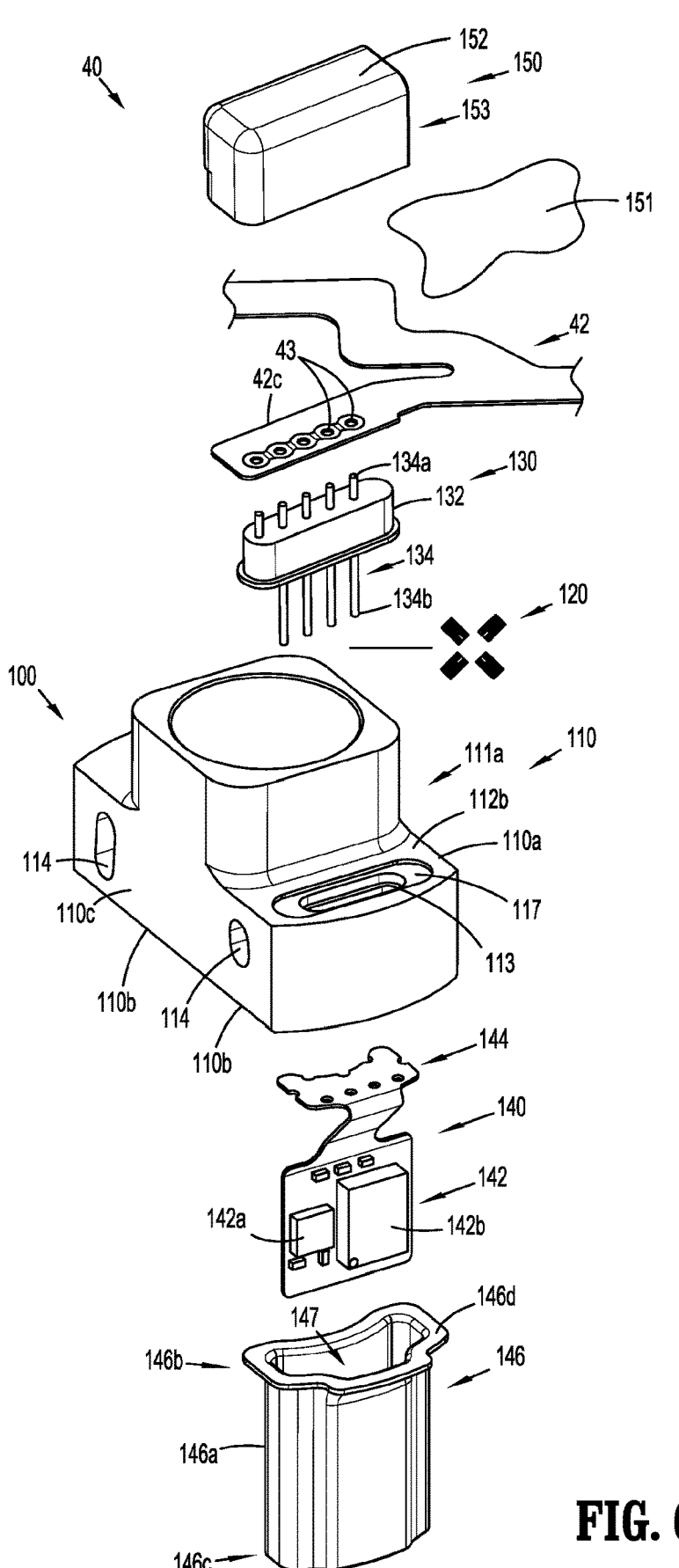
FIG. 6 is a perspective view of the electronic assembly of FIGS. 4 and 5, shown with parts separated.
Figure 7:
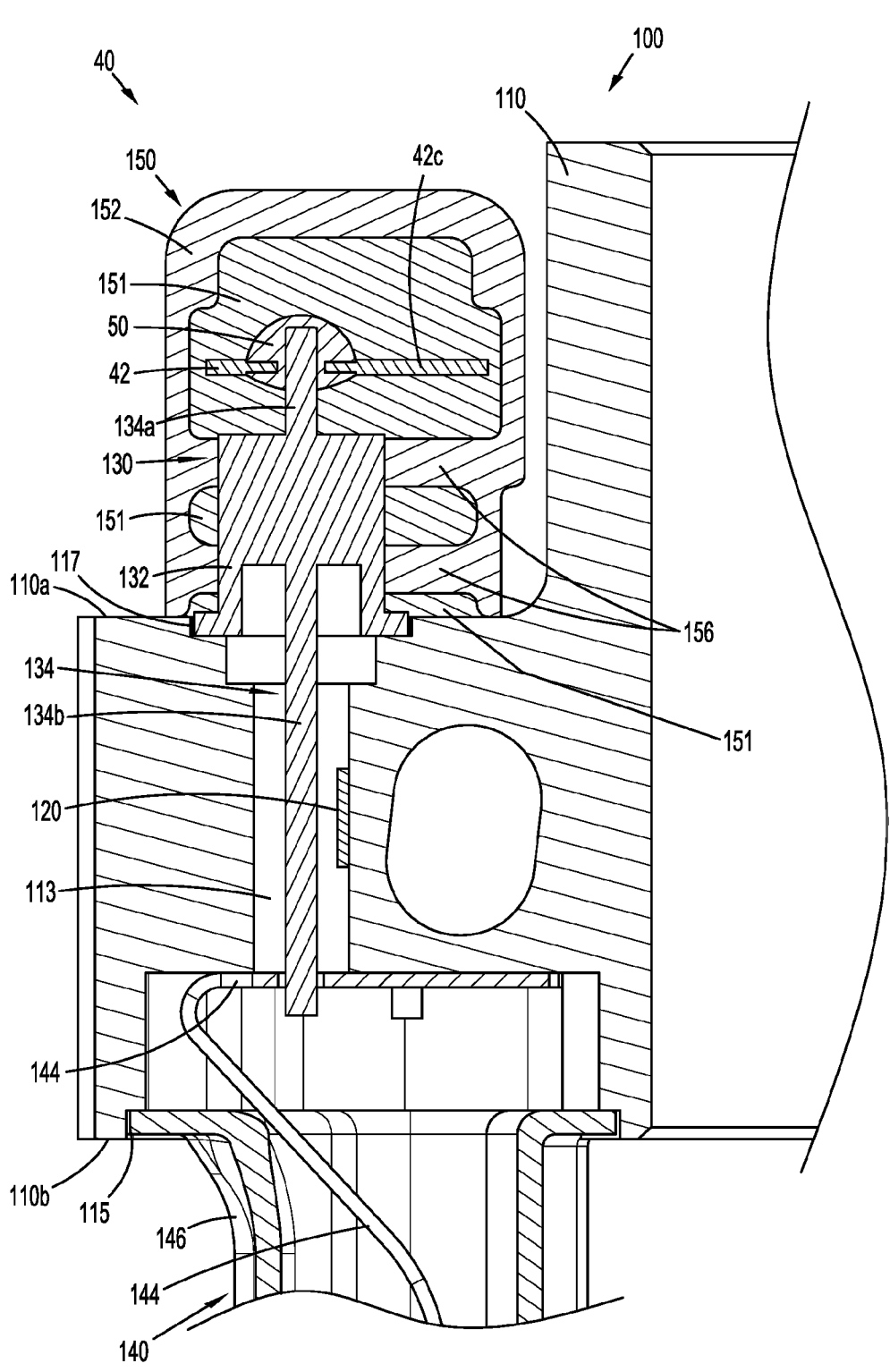
FIG. 7 is a cross-sectional view of the electronic assembly of FIGS. 4-6, taken along section line 7-7 of FIG. 4.

Turning now to FIGS. 6 and 7, the force sensor 100, the flex cable 42, and a seal assembly 150 of the electronic assembly 40 are shown. The force sensor 100 includes the substrate 110, sensing elements 120, a pin block assembly 130, and a chip assembly 140. The substrate 110 includes a cavity 113 defined in the first lateral half 111a that is open at both the proximal and distal surfaces 110a, 110b of the substrate 110. The distal surface 110a further includes a groove 115 (FIG. 7) recessed therein that extends around the opening into the cavity 113 for engagement with a housing 146 of the chip assembly 140.

In aspects, the substrate 110 includes relief holes 114 defined in a top surface 110c thereof to facilitate bending and/or to reduce stiffness of the substrate 110. It should be understood that the relief holes 114, as well as other relief features, such as relief cuts, may be formed in the substrate 110 in a variety of shapes and sizes, as well as in different positions about the substrate 110 when more elongation (e.g., flex) is desired.

The sensing elements 120, for example, strain gauges, are disposed within the cavity 113 of the substrate 110 and bonded (e.g., glued) to the substrate 110 along with associated components thereof (not shown), e.g., media layers, films, protective coatings, circuitry including electronic components, such as resistors, conductive wires and/or traces, and electronic and/or solder connectors, etc. The sensing elements 120 are connected together with a series of wires (not shown) to form a resistance bridge, e.g., a Wheatstone bridge, that can read a linear strain response of the substrate 110 when compressed, as is within the purview of those skilled in the art. Alternatively, the sensing elements 120 may be directly coated or etched onto the substrate 110 by, for example, vapor deposition. In some aspects, the substrate 110 includes a thin insulative layer (e.g., vapor deposited glass) and a thin conductive layer (e.g., nichrome) laser etched to include the sensing elements 120 and the Wheatstone bridge.

The pin block assembly 130 is fixedly secured to the substrate 110. The pin block assembly 130 includes a block body 132 and a plurality of pins 134 (referred to herein generally as pins) extending through the block body 132 in spaced relation relative to each other. The block body 132 is formed from an insulative material, such as glass or plastic, and the pins 134 are formed from a conductive material, such as metal. The proximal surface 110a of the substrate 110 includes a groove 117 recessed therein that extends around the opening into the cavity 113 for engagement with the block body 132 of the pin block assembly 130. Each of the pins 134 includes a proximal portion 134a and a distal portion 134b extending proximally and distally, respectively, from the block body 132. The proximal portions 134a of the pins 134 are exposed at the proximal surface 110a of the substrate 110 for electronic connection with the flex cable 42, and the distal portions 134b of the pins 134 are disposed within the cavity 113 of the substrate 110 for electronic connection with the sensing elements 120 (e.g., by wires (not shown)) and the chip assembly 140.

While the block body 132 is shown positioned atop the proximal surface 110a of the substrate 110, it should be understood that other arrangements are envisioned, such as a portion or the entirety of the block body 132 being positioned within the cavity 113 of the substrate 110 so long as the proximal portion 134a of the pins 134 are accessible (e.g., extend proximally outwardly beyond the proximal surface 110a of the substrate 110) for connection with the flex cable 42.

With continued reference to FIGS. 6 and 7, the chip assembly 140 includes a circuit board 142 and a connector 144 for electrical connection with the distal portions 134b of the pins 134 of the pin block assembly 130. The connector 144 is disposed within the cavity 113 of the substrate 110 and the circuit board 142 extends distally out of the cavity 113 beyond the distal surface 110b of the substrate 110. The circuit board 142 is configured for reading and/or storing data pertaining to the force sensor 100 and sending the data to the handle assembly 10 (FIG. 1) via the flex cable 42.

The circuit board 142 includes a microprocessor 142a and a memory 142b. The microprocessor 142a is configured to receive and/or measure electrical signals from the sensing elements 120 and record them in the memory 142b which, in turn, is configured to store the data received from the microprocessor 142a. The memory 142b is configured to communicate the data to the handle assembly 10 (FIG. 1) via electrical contact with the pin block assembly 130 and the flex cable 42 which, in turn, is electrically coupled to the handle assembly 10 by the first electrical connector 44 (FIG. 2). The data may be processed by a processor of the power-pack (not shown) of the handle assembly 10 (FIG. 1) or in some remote processor or the like. The data may include, for example, stress measurements along the anvil assembly 30 (FIG. 1) which are converted via an algorithm into corresponding tissue stress measurements. It should be understood that the data may correspond with other desired monitored properties of the end effector 20 (FIG. 1) which, in turn, correspond with other desired monitored tissue properties and/or behaviors depending upon the type of sensing elements 120 and/or sensor utilized in the anvil assembly 30.

The chip assembly 140 further includes a cover 146 sized and shaped to house the circuit board 142 therein. The cover 146 includes an elongated body 146a having an open proximal end 146b and a closed distal end 146c thereby defining a pocket 147 therein. A flange 146d extends around an entire outer perimeter of the open proximal end 146b for engagement with the distal surface 110b of the substrate 110 and, more specifically, for positioning within the groove 115 defined in the distal surface 110b. The cover 146 is positioned over the circuit board 142 and secured to the distal surface 110b of the substrate 110, e.g., by welding, adhesives, coatings, and/or mechanical connections to seal the cavity 113 on the distal surface 110b of the substrate 210. The cover 146 may be fabricated from a rigid material that is non-toxic, chemically inert, and capable of withstanding high temperatures and harsh detergents, such as, for example, a metal (e.g., stainless steel) or a polymer (e.g., polyphenylsulfone, such as those sold under the trademark RADEL® by Solvay Specialty Polymers USA, L.L.C.).

Alternatively, in some aspects, the circuit board 142, or components thereof, may be integrated into the flex cable 42. In such aspects, the chip assembly 140 may be otherwise omitted such that the cavity 113 of the substrate 110 is only open at the proximal surface 110a of the substrate 110.

The flex cable 42 is secured to the pin block assembly 130. The third portion 42c of the flex cable 42 is sized and shaped for positioning over the block body 132 of the pin block assembly 130 within the perimeter defined by the lateral wall 112b on which the pin block assembly 130 is positioned. The third portion 42c of the flex cable 42 includes a plurality of conductive holes 43 (referred to herein generally as conductive holes) defined therethrough that are sized, shaped, and positioned to mate with the pins 134 of the pin block assembly 130. The third portion 42c of the flex cable 42 is positioned over block body 132 such that the proximal portions 134a of the pins 134 of the pin block assembly 130 engage and extend through the conductive holes 43 of the flex cable 42. The flex cable 42 is soldered to the pins 134 at a plurality of solder connections 50 (FIG. 7, and referred to herein generally as solder connections) forming an electrical connection between the force sensor 100 and the flex cable 42.

With continued reference to FIGS. 6 and 7, the seal assembly 150 covers and seals the solder connections 50 as well as the cavity 113 of the substrate 110 to protect the flex cable 42, the pin block assembly 130, the sensing elements 120, the chip assembly 140, and the electronic connections between these electronic components so that the electronic components and electronic connections can operate in a wet environment e.g., after cleaning and sterilization cycles. The seal assembly 150 includes an encapsulate 151 and a housing 152. The housing 152 defines a chamber or cavity 153 therein that is sized and shaped to receive the third portion 42c of the flex cable 42 and the pin block assembly 130 therein, and is positionable against the substrate 110 to mate the housing 152 to the force sensor 100. The encapsulate 151 fills the housing 152 to cover the third portion 42c of the flex cable, the pin block assembly 130, and the solder connections 50 therebetween, as well as the interface between the pin block assembly 130 and the cavity 113 of the substrate 110 to further protect the electronic components and the electronic connections within the cavity 113 (e.g., the sensing elements 120, the distal portions 134b of the pins 134 of the pin block assembly 130, the circuit board 142, etc.).

The encapsulate 151 may be, for example, epoxies, silicones, urethanes, acrylics, among other materials that may form a strong bond and move with the thermal and mechanical movement of the flex cable 42 and/or the force sensor 100, and withstand cleaning and sterilization cycles. The encapsulate 151 may be, for example, resins or adhesives, such as those sold under the trademark LOCTITE® of Henkel IP & Holding GMBH (e.g., LOCTITE® 3301™), sealants, such as a room-temperature vulcanization (RTV) silicone, or conformal coating or potting materials, such as those sold under the trademarks HUMISEAL® of Columbia Chase Corporation or DOLPHON® of John C. Dolph Company. The encapsulate 151 may be a multi-component system (e.g., a two-part system) in which parts are kept isolated from one another and then combined to form the encapsulate 151, such as epoxy adhesives sold under the trademark SCOTCH-WELD® of 3M Company. The encapsulate 151 may be a material that cures upon application of a stimuli, such as heat, moisture, or exposure to light (e.g., ultraviolet light), such as acrylic light cure resins, which may be used with a translucent or transparent housing 152.

Figure 8:
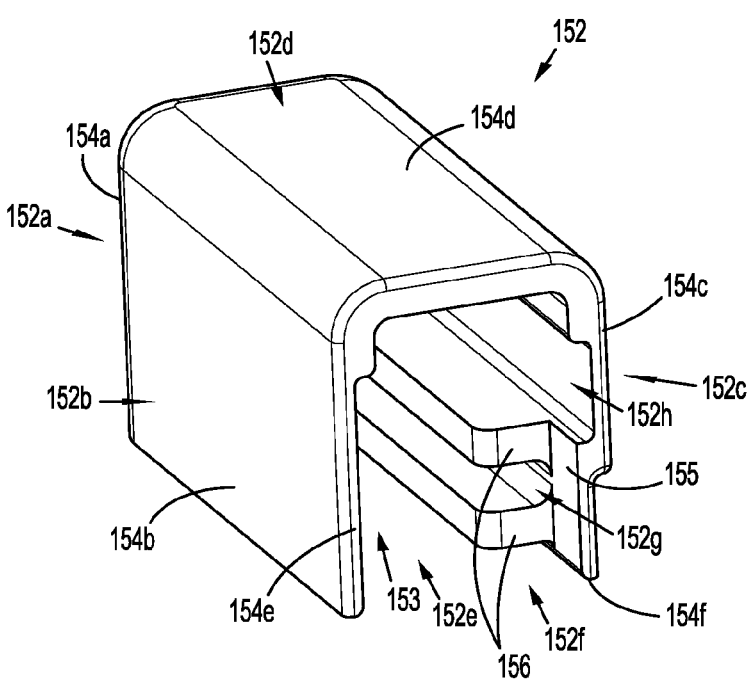
FIGS. 8 and 9 are perspective views of a housing of the seal assembly of FIGS. 4-7.
Figure 9:
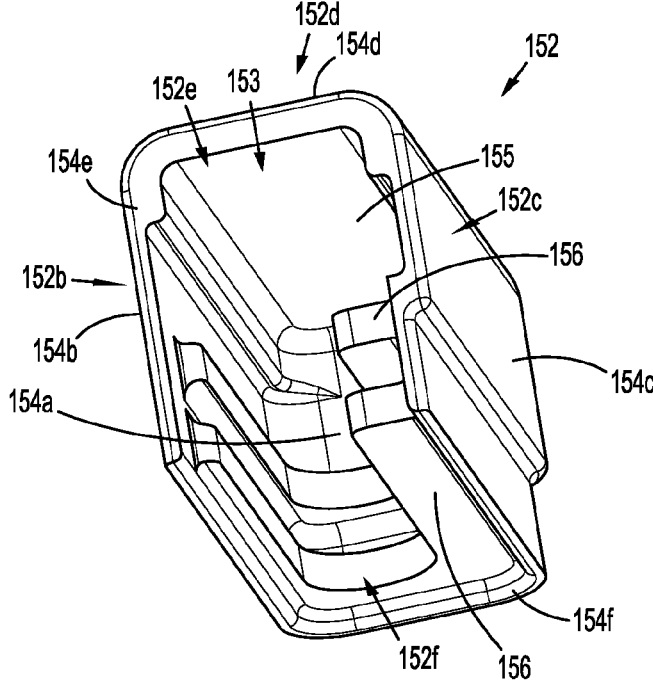

As shown in FIGS. 8 and 9, the housing 152 includes a first end wall 154a that defines a closed first end 152a of the housing 152, and first and second side walls 154b, 154c extending from the first end wall 154a in opposed spaced relation relative to each other. The first and second side walls 154b, 154c define closed first and second sides 152b, 152c of the housing 152. The housing 152 also includes top wall 154d extending over and interconnecting the first end wall 154a, the first side wall 154b, and the second side wall 154c. The top wall 154d defines a closed top 152d of the housing 152. The first end wall 154a, the first and second side walls 154b, 154c, and the top wall 154d are continuous surfaces to minimize exposure of electronic components positioned within the cavity 153 of the housing 152 to wet or harsh environments, however, it is envisioned that, in some aspects, openings, such as port or vent holes, or channels for the passage of electronic components (e.g., wires or cables), may be formed in one or more of the walls.

The housing 152 also includes an open second end 152e and an open bottom 152f. A second end surface 154c of the first side wall 154b, the second side wall 154c, and the top wall 154d define the open second end 152e, and a bottom surface 154f of the first end wall 154a, the first side wall 154b, and the second side wall 154c define the open bottom 152f. The open second end 152e and the open bottom 152f are open to the cavity 153 to allow the housing 152 to be placed over the solder connections 50 (FIG. 7). The bottom surface 154f is positionable against the substrate 110 (FIG. 6) of the force sensor 100 and the open second end 152e provides a passageway for the flex cable 42 (FIG. 6) out of the housing 152 and the encapsulate 151 (FIG. 7) into the cavity 153. The cavity 153 is defined by a continuous inner surface 155 of the first end wall 154a, the first and second side walls 154b, 154c, and the top wall 154d.

A lower portion 152g of the housing 152, extending from the bottom surface 154f towards the top wall 154d, includes a plurality of ribs 156 (referred to herein generally as ribs) extending from the inner surface 155 into the cavity 153. The ribs 156 are substantially u-shaped and extend from the first end wall 154a and the first and second side walls 154b, 154c. The ribs 156 are sized and positioned so that the portion of the cavity 153 defined within each of the ribs 156 corresponds with the shape of the block body 132 (FIG. 7) of the pin block assembly 130. In aspects, the ribs 156 form a slight interference fit with the block body 132 when the housing 152 is assembled thereover. In other aspects, other connections or fits are used between the block body 132 and the housing 152, such as snap fit, slip fit, and the like. While two ribs 156 are shown disposed in spaced relation relative to each other in the lower portion 152g of the housing 152, it should be understood that one rib 156 or more than two ribs 156 may be utilized that correspond in position, shape, and/or size with the electronic component to be encapsulated within the housing 152.

An upper portion 152h of the housing 152, disposed above the lower portion 152g, is sized and shaped to accommodate the third portion 42c (FIG. 6) of the flex cable 42 therein. In aspects, the upper portion 152h is sized and shaped so that the flex cable 42, the solder connections 50 (FIG. 7), and/or any exposed portion of the pins 134 are spaced from the inner surface 155 of the housing 152.

The housing 152 is formed from a material that is non-toxic, chemically inert, and capable of withstanding high temperatures and harsh detergents, such as, for example, metals (e.g., stainless steel), polymers (e.g., polyether ether ketone or polyphenylsulfone, such as those sold under the trademark RADEL® by Solvay Specialty Polymers USA, L.L.C.), resins (e.g., polyphenylene oxide or polyphenylene ether, such as those sold under the trademark NORYL® by SHPP Global Technologies B.V.), rubbers (e.g., silicones), and the like. The housing 152 may be formed from a translucent or transparent material to allow for light (e.g., UV or LED) to pass through the walls of the housing 152 to cure the encapsulate 151 (FIG. 7) within the housing 152. The housing 152 may be manufactured by, for example, molding (e.g., injection molding), machining, casting, stamping, and the like.

Figure 10:
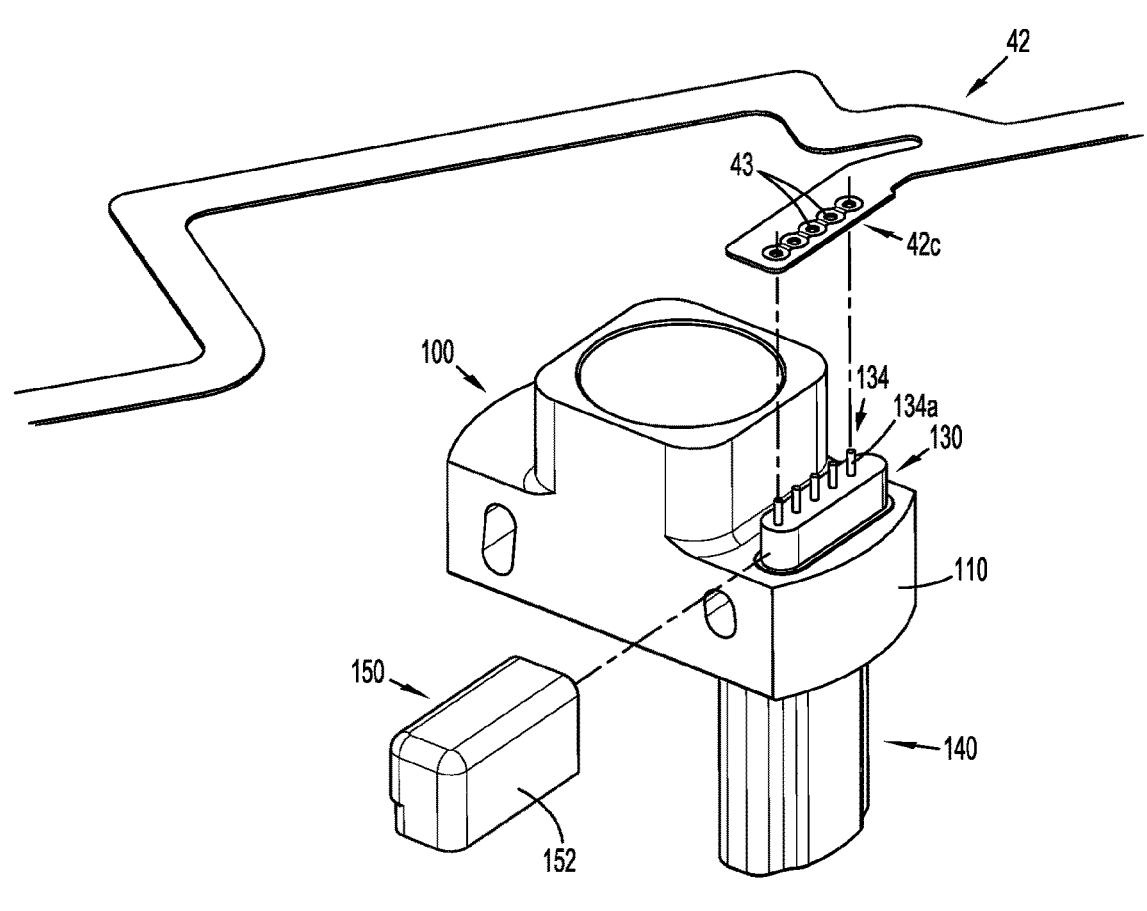
FIGS. 10-13 are perspective views of the electronic assembly of FIGS. 4-7, illustrating the assembly of the flex cable and the seal assembly to the force sensor in accordance with an aspect of the disclosure.
Figure 11:
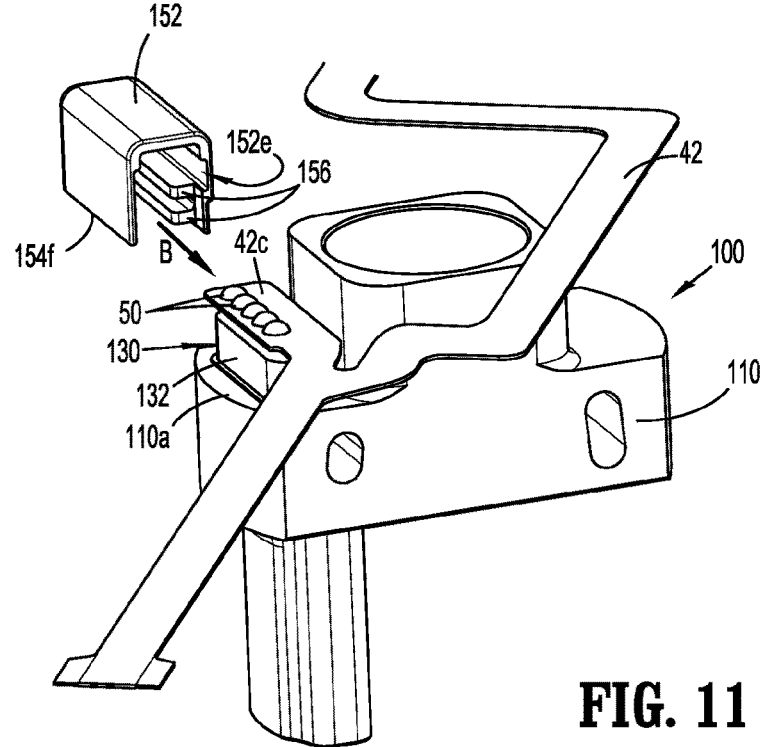

A method of assembling the flex cable 42 and the seal assembly 150 onto the force sensor 100 is shown in FIGS. 10-13. With the sensing elements 120 (FIG. 7), the pin block assembly 130, and the chip assembly 140 secured to the substrate 110, and the sensing elements 120 and the chip assembly 140 electrically coupled to the pin block assembly 130, as described above, the conductive holes 43 in the flex cable 42 are aligned with the proximal portions 134a of the pins 134 of the pin block assembly 130, as seen in FIG. 10. As seen in FIG. 11, the third portion 42c of the flex cable 42 is then placed atop the block body 132 of the pin block assembly 130 such that the proximal portions 134a (FIG. 10) of the pins 134 extend through the conductive holes 43 (FIG. 10) of the flex cable 42 and the flex cable 42 is soldered to the pins 134 at solder connections 50.

The housing 152 is then assembled onto the substrate 110 of the force sensor 100 and over the third portion 42c of the flex cable 42 and the pin block assembly 130. Initially, the bottom surface 154f of the housing 152 is aligned with the proximal surface 110a of the substrate 110 such that the open second end 152e of the housing 152 faces the flex cable 42 and the pin block assembly 130. The housing 152 is then slid in the direction of arrow B so that the ribs 156 wrap around the block body 132 (e.g., forming a slight interference fit) to register the assembly of the housing 152 onto the pin block assembly 130.

Figures 12, 13:
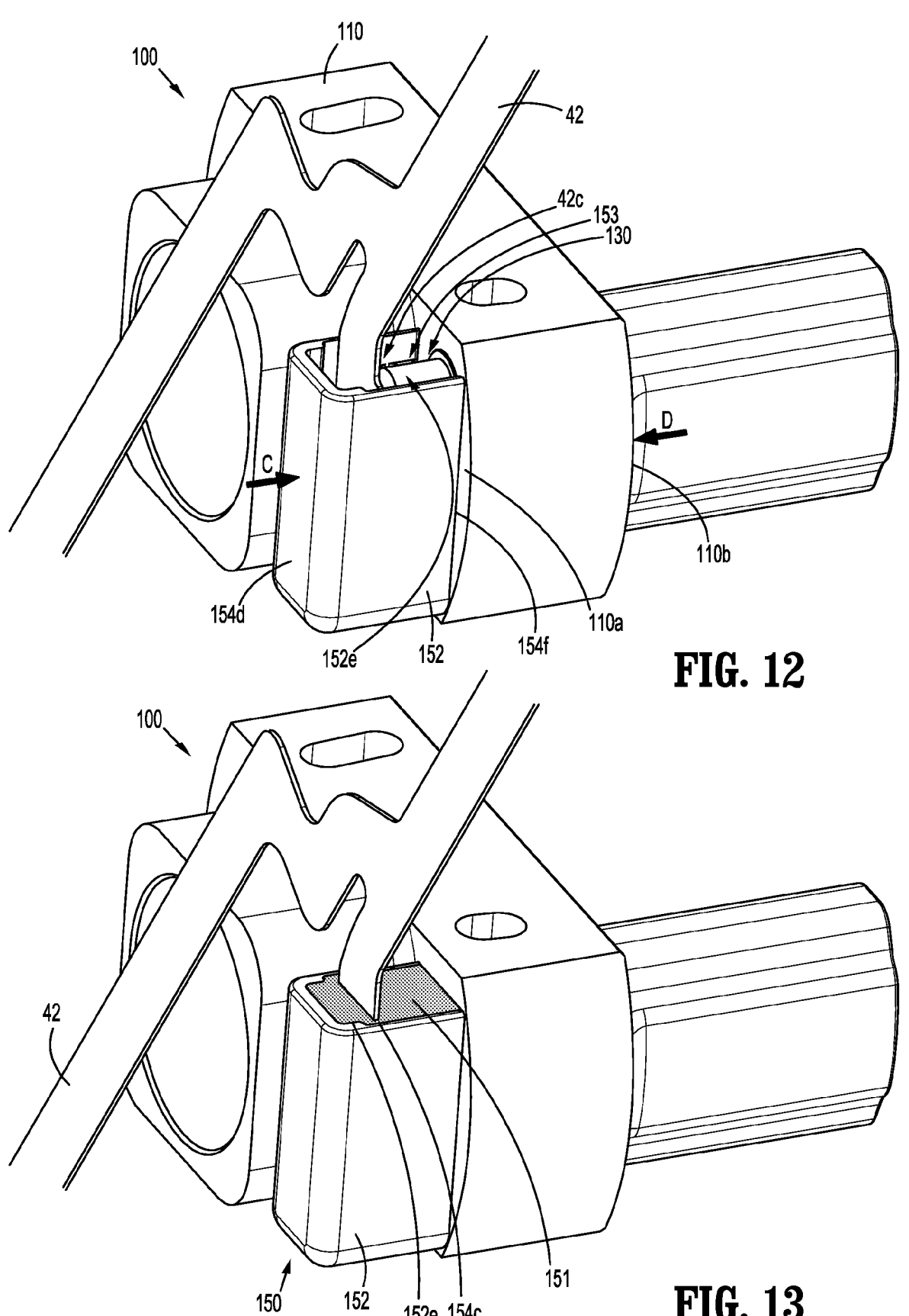

As seen in FIG. 12, the housing 152 is mated to the substrate 110 with the bottom surface 154f of the housing 152 in contact with the proximal surface 110a of the substrate 110 and the pin block assembly 130 and the third portion 42c of the flex cable 42 disposed within the cavity 153 of the housing 152. The flex cable 42 extends out of the open second end 152e of the housing 152. The housing 152 is clamped to the substrate 110 along clamp direction arrows C and D, forming a seal of the bottom surface 154f of the housing 152 to the substrate 110. This is achieved by applying clamping contact (e.g., via a clamp, vise, or press) along the top wall 154d of the housing 152 and a corresponding contact point on the distal surface 110b of the substrate 110.

In aspects, the seal is maintained by the clamp (not shown) so that the encapsulate 151 can be poured into the open second end 152e of the housing 152. Once the encapsulate 151 is cured, the clamp (not shown) is removed. In other aspects, the housing 152 is force mated with the substrate 110 by applying clamping contact, as described above, which forms a seal of the bottom surface 154f of the housing 152 to the substrate 110. Once clamped, an interference fit made between the housing 152 and the substrate 110 allows for the seal to be maintained once the clamp (not shown) is removed. This seal is maintained between the housing 152 and the substrate 110 by an interference fit (e.g., the interference fit created by the rib 156 (FIG. 11) or an interference fit created at the interface between the housing 152 and the substrate 110), or a gasket (see e.g., FIG. 20). In this manner, the clamp (not shown) can be removed prior to pouring of the encapsulate 151, if desired.

In aspects, the open second end 152e of the housing 152 is positioned upwards in a gravity opposed position, as seen in FIG. 12, so that the encapsulate 151 (FIG. 13) can be easily poured through the open second end 152e and into the cavity 153 for sealing the housing 152 to the substrate 110 and encapsulating the electronic components and the electronic connections disposed within the cavity 153.

As seen in FIG. 13, the encapsulate 151 is introduced into the cavity 153 (FIG. 12) of the housing 152 through the open second end 152e of the housing 152. The encapsulate 151 is rendered in a flowable (e.g., liquid) state for injecting or pouring the encapsulate 151 by any method suitable for the type of encapsulation material utilized, into the open second end 152e until the encapsulate 151 fills the cavity 153 and, as seen in FIG. 7, fully covers the pin block assembly 130, the third portion 42c of the flex cable 42, and the solder connections 50 therebetween, as well as the interface of the pin block assembly 130 with the cavity 113 of the substrate 110. Once filling is complete, the encapsulate 151 is allowed to solidify and/or cure, the clamp (not shown) is removed, and the electronic assembly 40 is ready for use. In aspects utilizing an encapsulate 151 that cures upon application of a stimuli, the appropriate stimuli is applied to the seal assembly 150. For example, in the case of light cured resins, light may be applied to the housing 152 to cure the encapsulate 151 disposed therein.

Once the encapsulate 151 is cured, only the portion or face of the encapsulate 151 sealing closed the open second end 152e of the housing 152 is exposed to wet or harsh environments. The remaining portion of the encapsulate 151 is protected by walls of the housing 152 which are formed from a material chosen to be impervious to wet and harsh environments, as discussed above. In some aspects, the housing 152 may be sized to allow for increased depth of the encapsulate 151 so that multiple cleaning and sterilization cycles can only attack a minimal thickness of the encapsulate 151. Such aspects provide a margin of safety and may allow for the selection of lower cost encapsulates. Additionally, or alternatively, the second end surface 154e of the housing 152 may be increased to further minimize the amount of the encapsulate 151 exposed to wet or harsh environments.

Turning now to FIGS. 14-20, an electronic assembly 40a in accordance with another aspect of this disclosure is shown for use in the surgical device 1 (FIG. 1). The electronic assembly 40a is substantially similar to the electronic assembly 40 (FIG. 4) and includes a flex cable 42, a force sensor 100, and a seal assembly 250. The seal assembly 250 is utilized to encapsulate and seal the third portion 42c of the flex cable 42, the pin block assembly 130, and the electronic connections therebetween, as well as the interface between the pin block assembly 130 and the cavity 113 (FIG. 20) of the substrate 110 to protect the electronic components and electronic connections disposed within the seal assembly 250 and the cavity 113.

Figure 14:
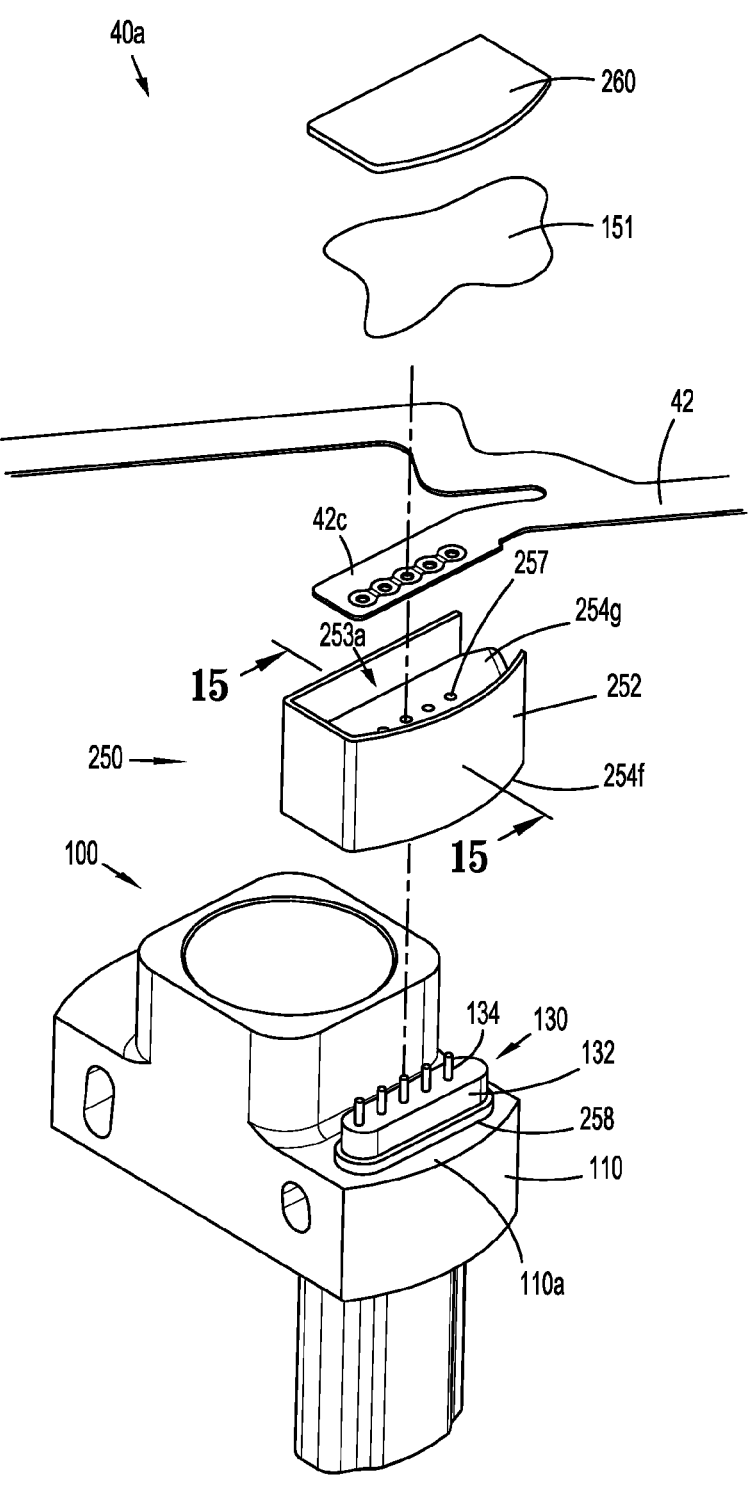
FIG. 14 is a perspective view of an electronic assembly in accordance with another aspect of the disclosure, the electronic assembly including a force sensor, a flex cable, and a seal assembly, shown with these parts separated.
Figure 20:
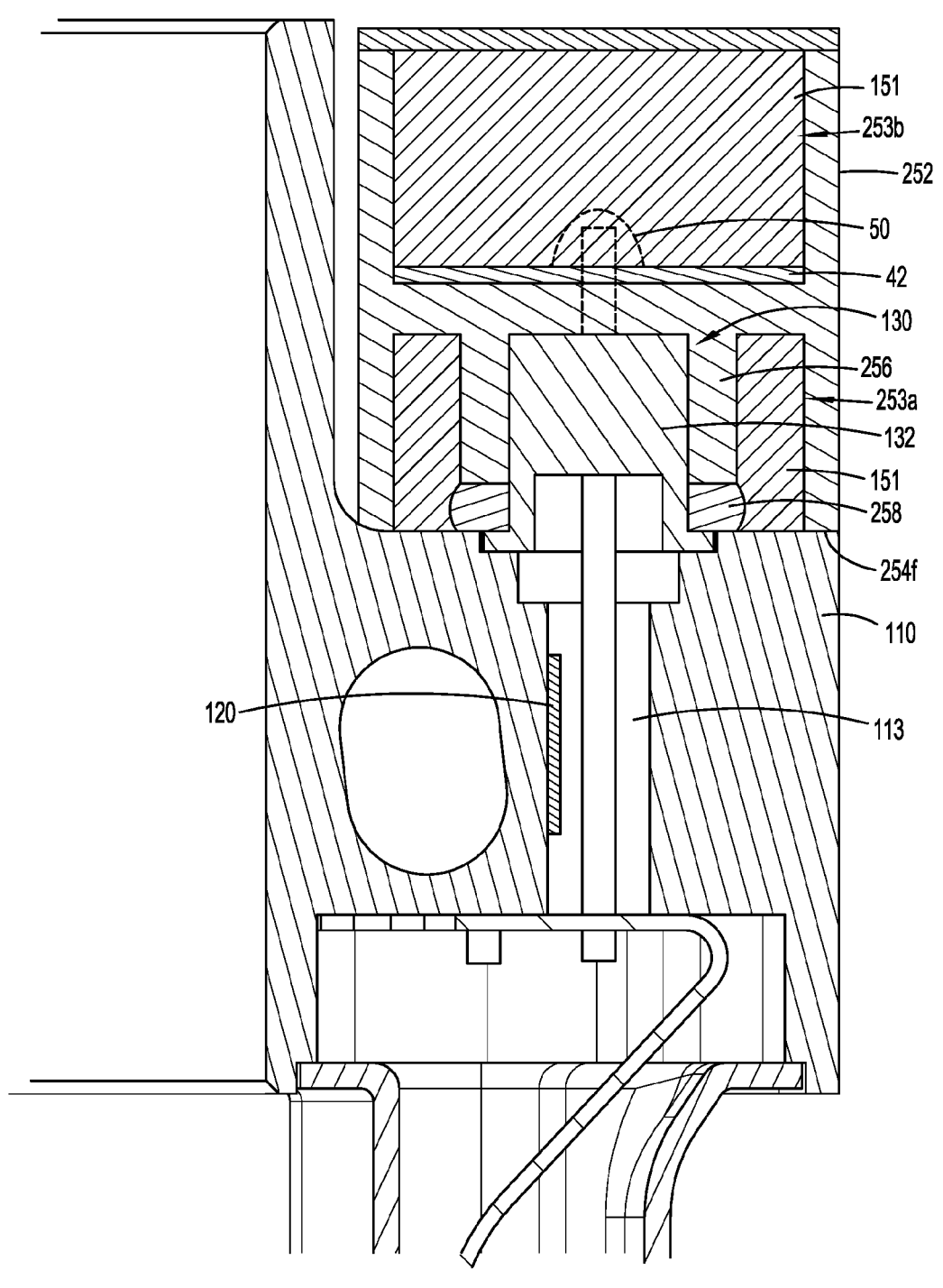
FIG. 20 is a cross-sectional view of the electronic assembly of FIG. 19, shown in a fully assembled state, taken along section line 20-20 of FIG. 19.

The seal assembly 250 includes an encapsulate 151, a housing 252, a gasket 258, and a top plate 260. As seen in FIG. 14, the gasket 258 is positioned around the block body 132 of the pin block assembly 130 and against the proximal surface 110a of the substrate 110. The gasket 258 is formed from a compliant material, such as an elastomeric material (e.g., silicone, rubber, or combinations thereof, such as those sold under the trademark ELASTOSIL® of Wacker Chemie AG) that is compressible to aid in sealing the opening into the cavity 113 of the substrate 110. As seen in FIG. 20, the gasket 258 forms a seal between the interface of the block body 132 and the substrate 110 to protect the electronic components (e.g., the sensing elements 120) disposed within the cavity 113 of the substrate 110 from exposure to wet or harsh environments.

Figure 15:
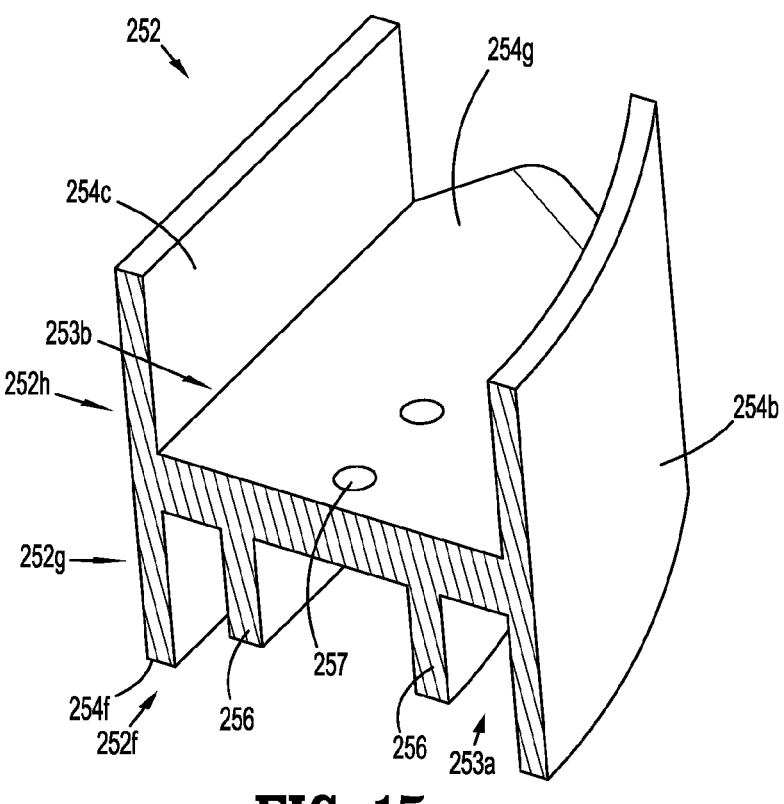
FIG. 15 is a partial cross-sectional view of a housing of the seal assembly of FIG. 14, taken along section line 15-15 of FIG. 14.
Figure 16:
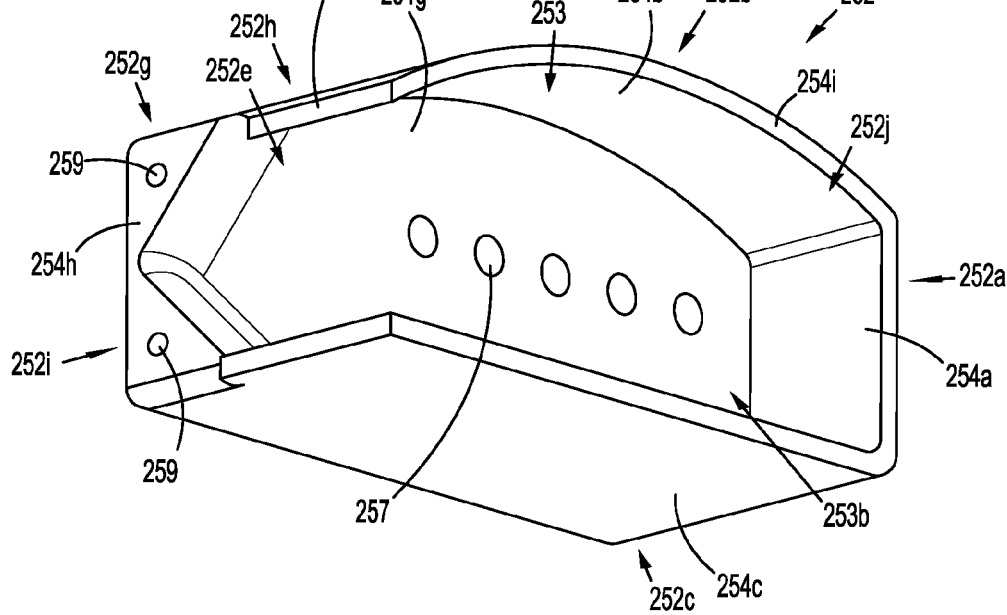
FIG. 16 is a top, perspective view of the housing of the seal assembly of FIGS. 14 and 15.

As seen in FIGS. 15 and 16, the housing 252 includes a first end wall 254a that defines a closed first end 252a of the housing 252, and first and second side walls 254b, 254c extending from the first end wall 254a in opposed spaced relation relative to each other. The first and second side walls 254b, 254c define closed first and second sides 252b, 252c of the housing 252. The housing 252 also includes an intermediate wall 254g disposed within a cavity 253 defined within the first end wall 254a, the first side wall 254b, and the second side wall 254c. The intermediate wall 254g separates lower and upper portions 252g, 252h of the housing 252 and divides the cavity 253 into lower and upper cavity portions 253a, 253b.

The intermediate wall 254g defines openings 257 therethrough that are in open communication with the lower and upper cavity portions 253a, 253b of the housing 252. The openings 257 are configured and dimensioned to receive the pins 134 (FIG. 14) of the pin block assembly 130 therethrough. A rib 256 extends from the intermediate wall 254g into the lower cavity portion 253a defined in the lower portion 252g of the housing 252. The rib 256 corresponds in shape with the gasket 258 (FIG. 20) and is configured to abut the gasket 258 when the housing 252 is positioned on the substrate 110.

The lower portion 252g of the housing 252 is sized and shaped to accommodate the pin block assembly 130 (FIG. 14) therein. The lower portion 252g includes a second end wall 254h that defines a substantially closed second end 252i of the lower portion 252g of the housing 252 but for holes 259 extending through the second end wall 254h such that each of the holes 259 is in fluid communication with the lower cavity portion 253a and the outside environment. In aspects, the holes 259 are utilized as port holes to fill the lower cavity portion 253a with the encapsulate 151 (FIG. 14). In other aspects, one of the holes 259 is used as a port hole and another of the holes 259 is utilized as a vent hole during filling of the encapsulate 151 into the cavity 253. It should be understood that the number and location of the holes 259 may vary (e.g., only one hole may be provided in the second end wall 254h). The lower portion 252g of the housing 252 also includes an open bottom 252f. A bottom surface 254f of the first and second end walls 254a, 254h and the first and second side walls 254b, 254c define the open bottom 254f. The open bottom 254f allows the housing 252 to be placed over the pin block assembly 130 and against the substrate 110.

The upper portion 252h of the housing 252 is sized and shape to accommodate the third portion 42c (FIG. 18) of the flex cable 42 and the solder connections 50 (FIG. 18) therein. The upper portion 252h includes an open second end 252e and an open top 252j. A second end surface 254e of the first side wall 254b, the second side wall 254c, and the intermediate wall 254g define the open second end 252e, and a top surface 254i of the first end wall 254a, the first side wall 254b, and the second side wall 254c define the open top 252j. The open top 252j allows the flex cable 42 (FIG. 18) to be positioned into the housing 252 and soldered to the pin block assembly 130 (FIG. 17), and the open second end 252e provides a passageway for the flex cable 42 out of the housing 152 and the encapsulate 151 (FIG. 14) into the upper cavity portion 153b. The top plate 260 (FIG. 14) is configured for positioning over the top surface 254*i* of the housing 252 to close the open top 252*j*.

Figures 17, 18:
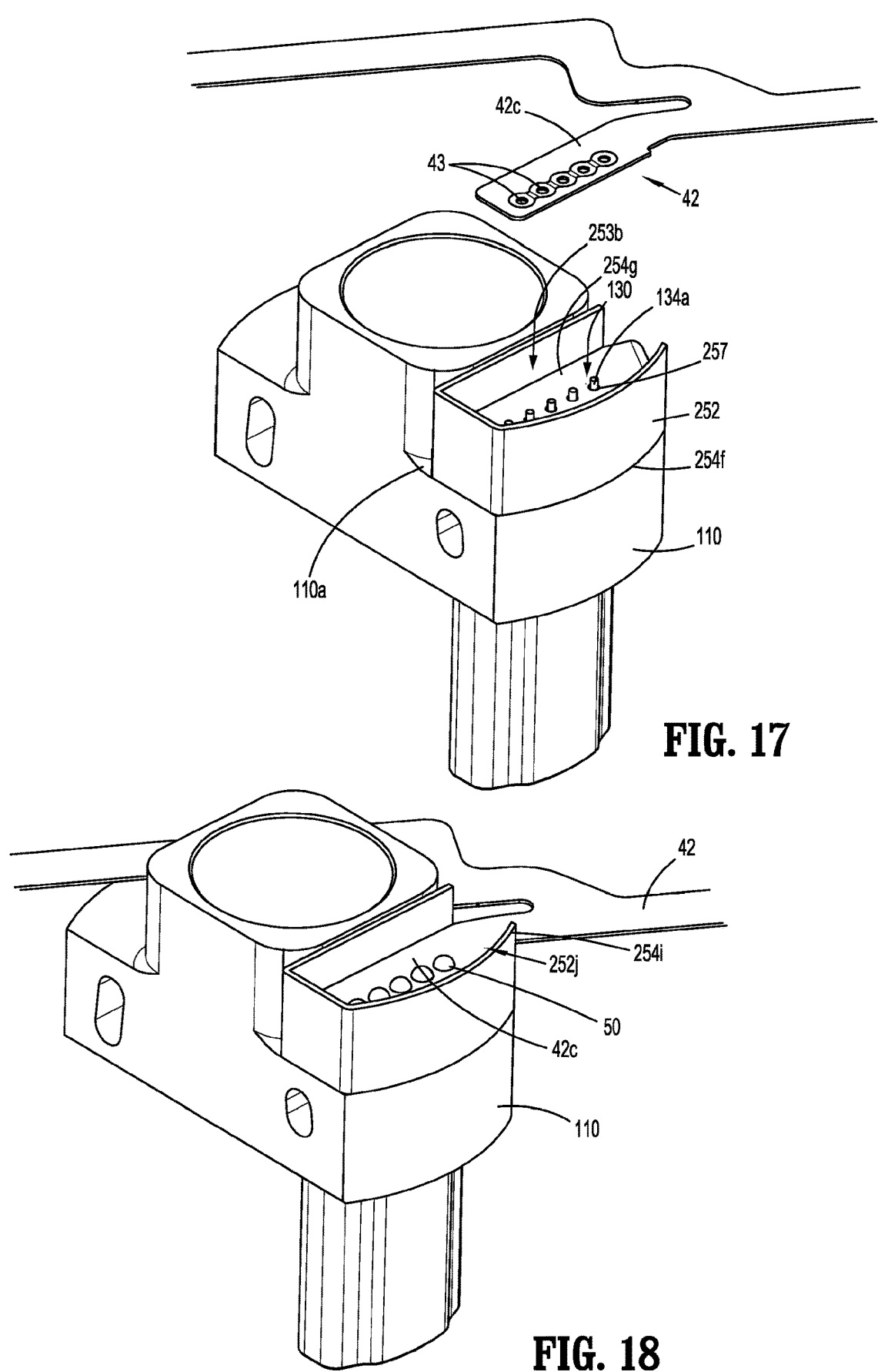
FIGS. 17-19 are perspective views of the electronic assembly of FIG. 14, illustrating the assembly of the flex cable and the seal assembly to the force sensor in accordance with an aspect of the disclosure.

In a method of assembling the flex cable 42 and the seal assembly 250 onto the force sensor 100, as initially seen in FIG. 14, the housing 252 is aligned over the pin block assembly 130, on which the gasket 258 is already positioned, with the bottom surface 254*f* of the housing 252 facing the proximal surface 110*a* of the substrate 110 and the openings 257 in the intermediate wall 254*g* aligned with the pins 134 of the pin block assembly 130. As seen in FIG. 17, the housing 252 is then placed atop the block body 132 (FIG. 14) of the pin block assembly 130 such that the proximal portions 134*a* of the pins 134 extend through the openings 257 defined in the intermediate wall 254*g* and the bottom surface 254*f* is in contact with the proximal surface 110*a* of the substrate 110. As seen in FIG. 20, the block body 132 of the pin block assembly 130 is disposed within the lower cavity portion 253*a* of the housing 252. Upon positioning of the housing 252 over the pin block assembly 130, the rib 256 of the housing 252 contacts and compresses the gasket 258 and seals the gasket 258 against the substrate 110. In aspects, the housing 252 is clamped onto the substrate 110 of the force sensor 100 so that the rib 256 compresses the gasket 258 when the bottom surface 254*f* of the housing 252 contacts the substrate 110 during clamping. Those skilled in the art can appreciate that any compression distance is possible. In some aspects, the gasket 258 is compressed about 0.01" to about 0.05" and, in certain aspects, about 0.03", although any compression distance is contemplated.

With continued reference to FIG. 17, the conductive holes 43 in the flex cable 42 are then aligned with the proximal portions 134*a* of the pins 134 of the pin block assembly 130 extending into the upper cavity portion 253*b* of the housing 252 and the third portion 42*c* of the flex cable 42 is then placed atop the intermediate wall 254*g* within the upper cavity portion 253*b* such that the proximal portions 134*a* of the pins 134 extend through the conductive holes 43 of the flex cable 42. As seen in FIG. 18, the flex cable 42 is soldered to the pins 134 (FIG. 17) at solder connections 50. In aspects, placement of the third portion 42*c* of the flex cable 42 into the housing 242 and soldering of the flex cable 42 to the pin block assembly 130 are performed while the housing 252 is clamped to the substrate 110 so that the flex cable 42 is maintained in a stress free state.

Figure 19:
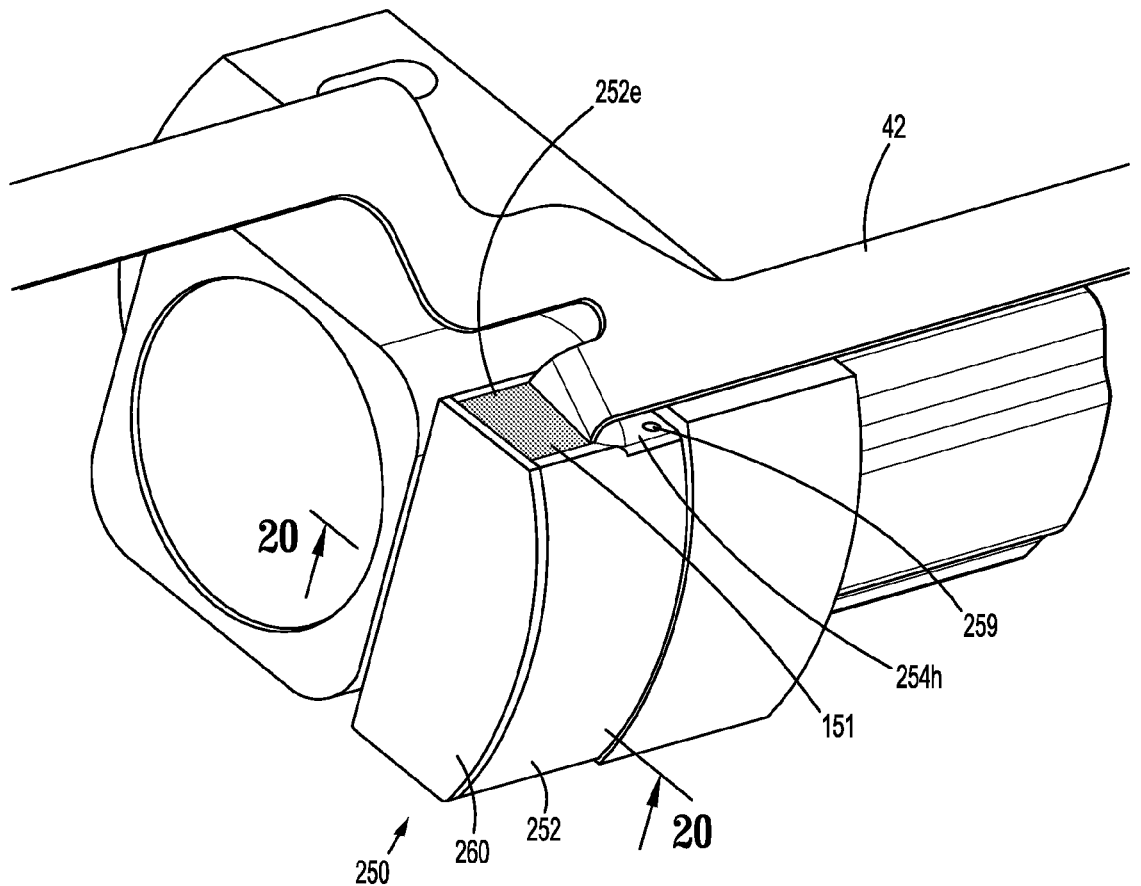

As seen in FIG. 19, the top plate 260 is placed over the open top 252*j* (FIG. 18) of the housing 252 and against the top surface 254*i* (FIG. 18) to enclose the open top 252*j*. The top plate 260 is then clamped onto housing 252. Alternatively, in some aspects, the top plate 260 may be pre-formed as part of the housing 252 and the flex cable 42 introduced into the upper cavity portion 253*b* of the housing 252 through the open second end 252*e*. The open second end 252*e* of the housing 252, through which the flex cable 42 extends, is then positioned upwards in a gravity opposed position so that the encapsulate 151 can be easily poured or injected into the holes 259 and the open second end 252*e* to fill the lower and upper cavity portions 253*a*, 253*b* (FIG. 20) of the housing 252.

Once filling is complete, the encapsulate 151 is allowed to solidify and/or cure, the clamp (not shown) is removed, and the electronic assembly 40*a* is ready for use. Once the encapsulate 151 is cured, only the portions of the encapsulate 151 sealing closed the open second end 252*e* and the holes 259 in the housing 152 is exposed to wet or harsh environments.

Figures 25, 26:
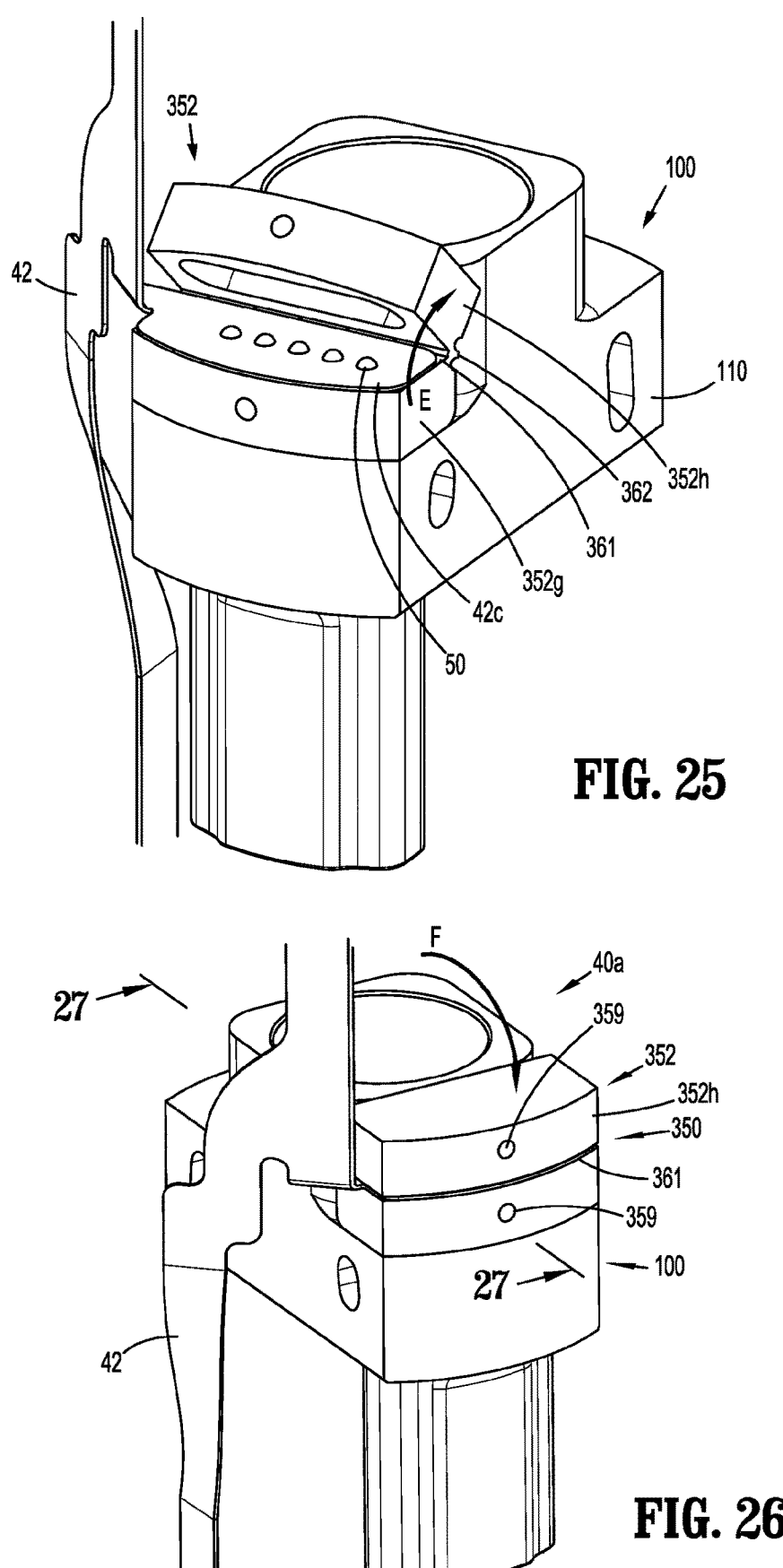
Figure 27:
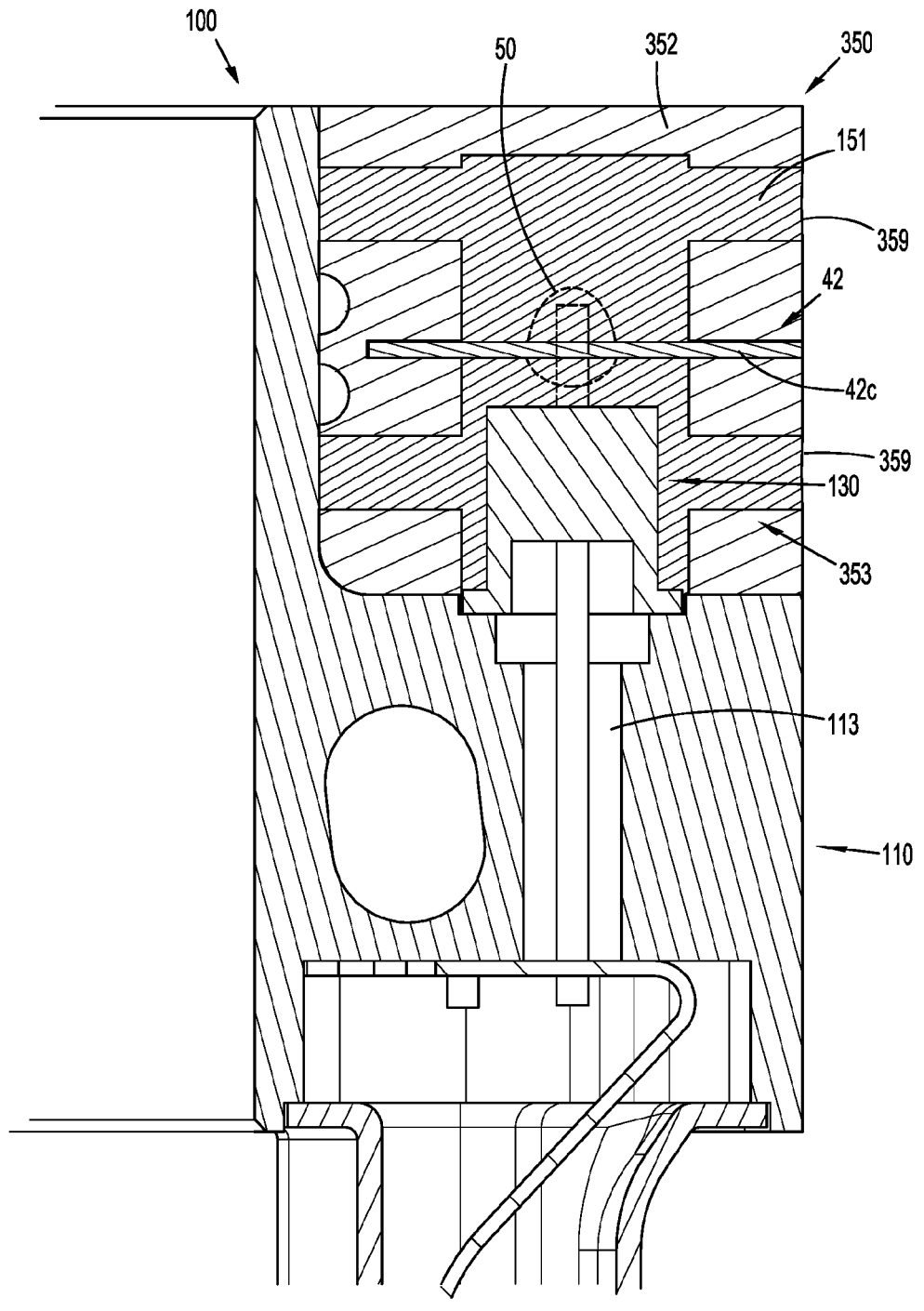
FIG. 27 is a cross-sectional view of the electronic assembly of FIG. 26, shown in a fully assembled state, taken along section line 27-27 of FIG. 26.

Turning now to FIGS. 21-27, an electronic assembly 40*b* (FIG. 26) in accordance with another aspect of this disclosure is shown for use in the surgical device 1 (FIG. 1). As seen in FIGS. 26 and 27, the electronic assembly 40*b* is substantially similar to the electronic assembly 40 (FIG. 4) and includes a flex cable 42, a force sensor 100, and a seal assembly 350. The seal assembly 350 is utilized to encapsulate and seal the third portion 42*c* of the flex cable 42, the pin block assembly 130, and the electronic connections therebetween, as well as the interface between the pin block assembly 130 and the cavity 113 of the substrate 110 to protect the electronic components and electronic connections disposed within the seal assembly 350 and the cavity 113.

Figure 21:
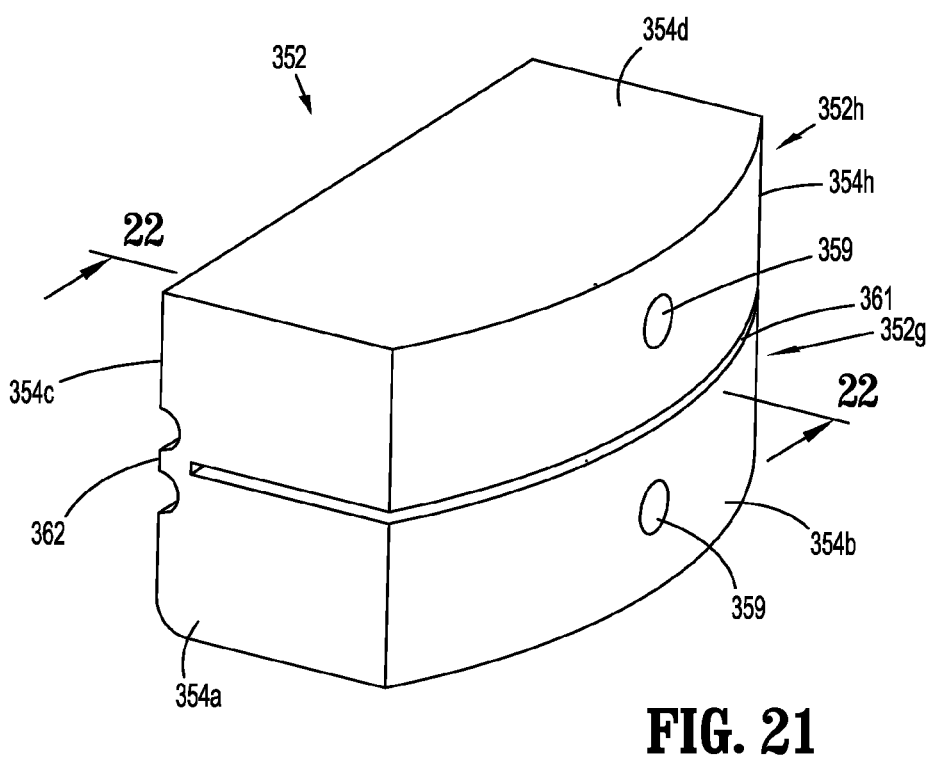
FIG. 21 is a perspective view of a housing of a seal assembly in accordance with another aspect of the disclosure.
Figure 22:
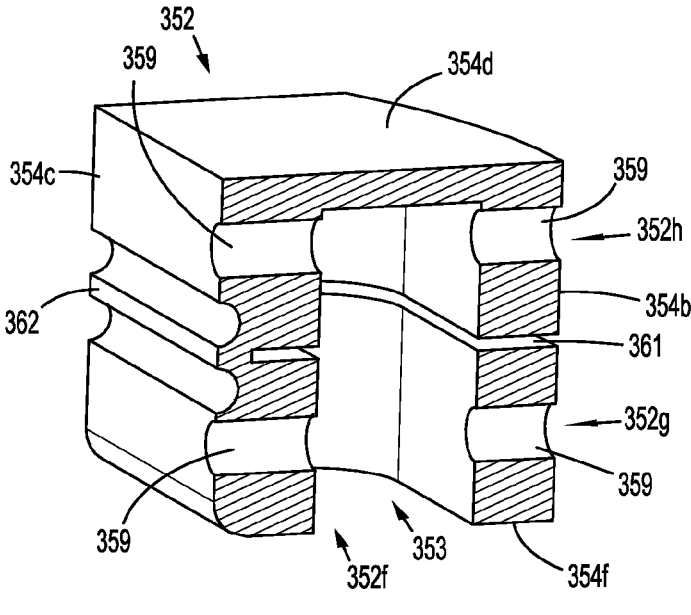
FIG. 22 is a cross-sectional view of the housing of FIG. 21, taken along section line 22-22 of FIG. 21.

The seal assembly 350 includes an encapsulate 151 and a housing 352. As seen in FIGS. 21 and 22, the housing 352 includes a first end wall 354*a*, first and second side walls 354*b*, 354*c*, a second end wall 354*h*, and a top wall 354*d*. The housing 352 defines a cavity 353 therein and includes an open bottom 352*f*. A bottom surface 354*f* of the first end wall 354*a*, the first and second side walls 354*b*, 354*c*, and the second end wall 354*h* define the open bottom 352*f*. Holes 359 extend through the first and second side walls 354*b*, 354*c* and are in fluid communication with the cavity 353 and the outside environment. The holes 359 are utilized as port holes for filling the cavity 353 with the encapsulate 151 (FIG. 27) from multiple directions. It should be understood that any number of holes 359 may be utilized to fill the cavity 353 (e.g., a single hole 359 may be used) and the location of the hole(s) 359 may also vary (e.g., hole(s) may be defined in the top wall 354*d*).

A substantially u-shaped slit 361 extends partially through each of the first and second end walls 354*a*, 354*h* and the entirety of the first side wall 354*b* and bifurcates the housing 352 into lower and upper portions 352*g*, 352*h*. A hinge 362 is defined in the second side wall 354*c* along the same plane as the slit 361 so that the upper portion 352*h* of the housing 352 is movable relative to the lower portion 352*g* about the hinge 362 between a closed position, as seen in FIGS. 21 and 22, and an open position, as shown in FIG. 25. The hinge 362 is a living hinge that is biased to retain the housing 352 in the closed position, such that a separation force is needed to move the housing 352 to the open position. When the separation force is removed, the resilience of the hinge 362 returns the housing 352 to the closed position. When the housing 352 is in the closed position, the slit 361 is dimensioned to mate with the flex cable 42.

While the hinge 362 is shown as a living hinge, it should be understood that other hinge configurations are envisioned, such as a pivot pin extending through aligned apertures defined in the lower and upper portions 352*g*, 352*h* of the housing 352. Accordingly, the hinge 362 may be integrally formed with the housing 352, or may be a separate component pivotably connecting the lower and upper portions 352*g*, 352*h* of the housing 352.

Figures 23, 24:
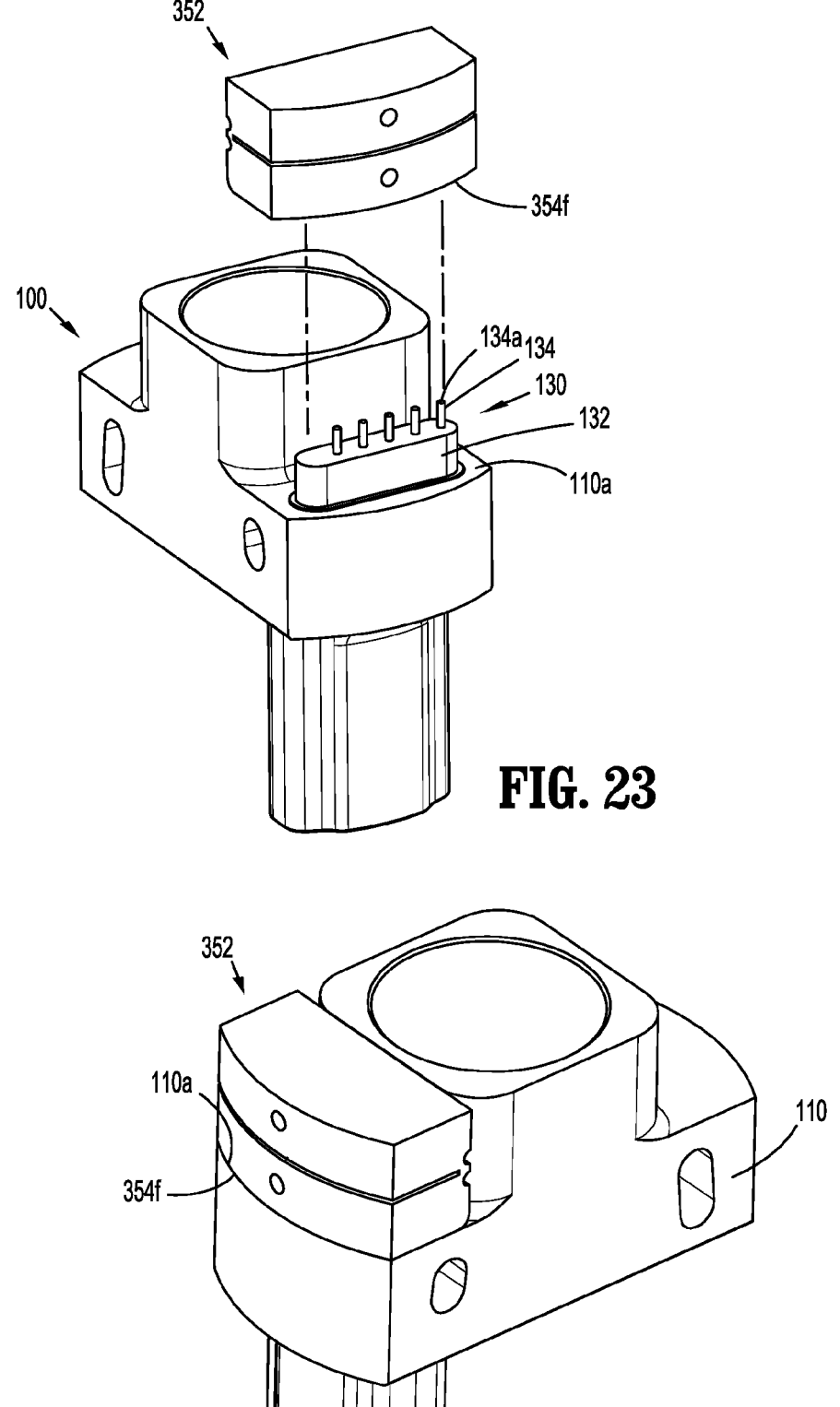
FIGS. 23-26 are perspective views illustrating the assembly of an electronic assembly including a flex cable, a force sensor, and a seal assembly including the housing of FIG. 21 in accordance with an aspect of the disclosure.

In a method of assembling the flex cable 42 and the seal assembly 350 onto the force sensor 100, as initially seen in FIG. 23, the housing 352 is aligned over the pin block assembly 130 with the bottom surface 354*f* of the housing 352 facing the proximal surface 110*a* of the substrate 110. The housing 352 is then placed over the pin block assembly 130, as seen in FIG. 24, such that the bottom surface 354*f* of the housing 352 contacts the proximal surface 110*a* of the substrate 110 and the pin block assembly 130 is disposed within the cavity 353 (FIG. 22) of the housing 352. As seen in FIG. 25, the housing 352 is then moved to the open position by flexing the upper portion 352*h* of the housing 352 along the hinge 362 (e.g., pivoting the upper portion 352*h* in the direction of arrow E) to enlarge the slit 361 and create an opening large enough to allow the third portion 42c of the flex cable 42 to be positioned within the slit 361 between the lower and upper portions 352g, 352h. The flex cable 42 is placed atop the block body 132 (FIG. 23) of the pin block assembly 130 with the proximal portions 134a of the pins 134 extending through the conductive holes 43 of the flex cable 42, and the flex cable 42 is soldered to the pins 134 at solder connections 50. As seen in FIG. 26, the upper portion 352h of the housing 352 is released or pivoted back in the direction of arrow F to the closed position to capture the flex cable 42 within the slit 361 of the housing 352.

As seen in FIG. 27, the encapsulate 151 is then injected into the holes 359, for example, with a fill apparatus such as a syringe, to fill the cavity 353 of the housing 352. Once filling is complete, the encapsulate 151 is allowed to solidify and/or cure and the electronic assembly 40b is ready for use. Once the encapsulate 151 is cured, only the portions of the encapsulate 151 sealing closed the holes 359 in the housing 352 is exposed to wet or harsh environments.

Turning now to FIGS. 28-32, an electronic assembly 40c in accordance with another aspect of this disclosure is shown for use in the surgical device 1 (FIG. 1). The electronic assembly 40c is substantially similar to the electronic assembly 40 (FIG. 4) and includes a flex cable 42, a force sensor 100, and a seal assembly 450. The seal assembly 450 is utilized to encapsulate and seal the third portion 42c of the flex cable 42, the pin block assembly 130, and the electronic connections therebetween, as well as the interface between the pin block assembly 130 and the cavity 113 (FIG. 32) of the substrate 110 to protect the electronic components and electronic connections disposed within the seal assembly 450 and the cavity 113.

The seal assembly 450 includes a housing 452 integrated onto the third portion 42c of the flex cable 42. In aspects, the housing 452 is overmolded onto the flex cable 42. The housing 452 is formed from a compliant material that can withstand harsh environments, such as an elastomeric material (e.g., silicone, rubber, or combinations thereof, such as those sold under the trademark ELASTOSIL® of Wacker Chemie AG) that is compressible and forms a seal with a surface to which it is mated.

Figure 29:
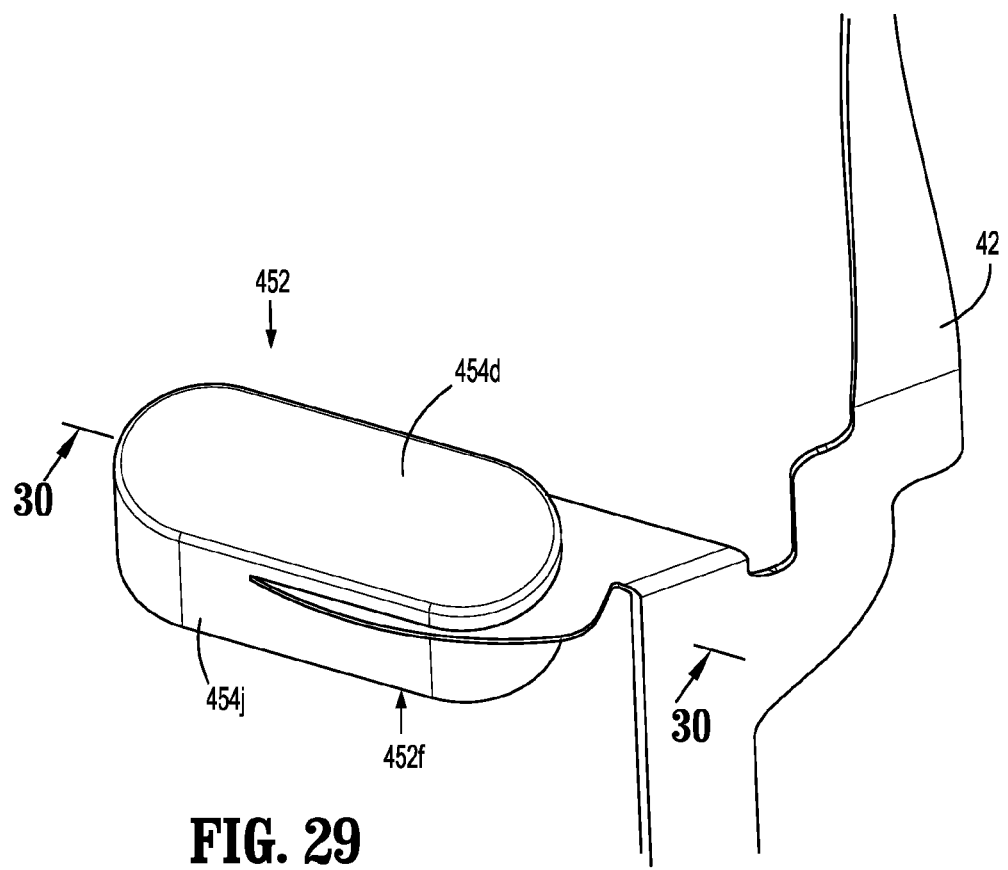
FIG. 29 is a perspective view of the flex cable and integrated housing of FIG. 28.
Figure 30:
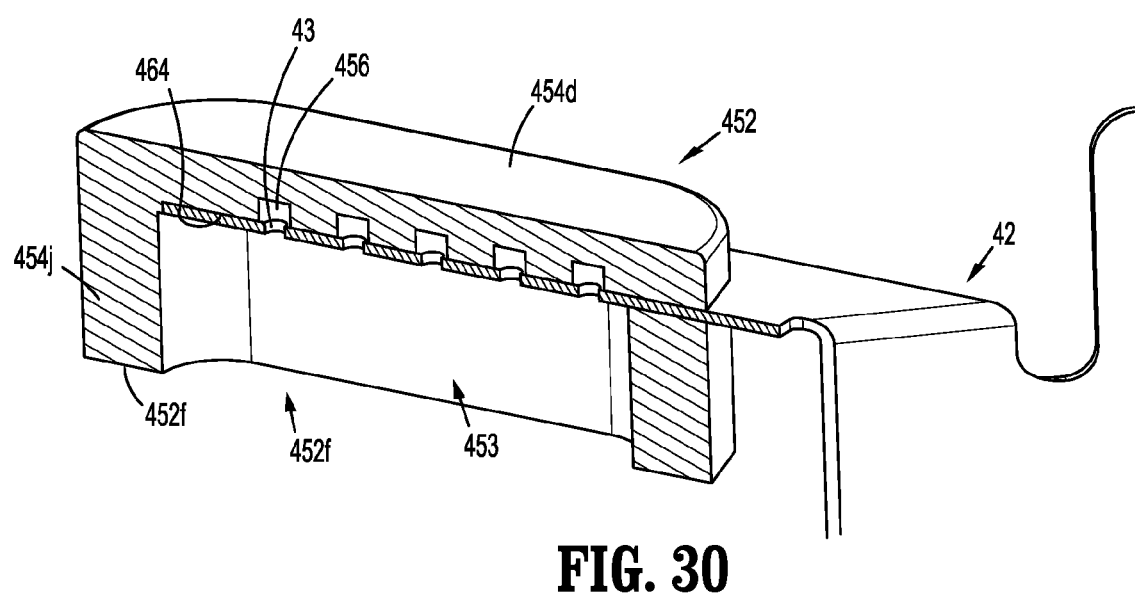
FIG. 30 is a cross-sectional view of the flex cable and integrated housing of FIGS. 28 and 29, taken along section line 30-30 of FIG. 29.

As seen in FIGS. 29 and 30, the housing 452 includes a top wall 454d, a side wall 454j extending continuously around the housing 452 and defining a closed perimeter around a cavity 453 defined in the housing 452, and an open bottom 452f defined by a bottom surface 454f of the side wall 454j. An inner surface 464 of the top wall 454d includes a plurality of grooves 465 (referred to herein generally as grooves) defined therein that are aligned with the conductive holes 43 defined through the flex cable 42. The housing 452 is overmolded onto the flex cable 42 such that the flex cable 42 is positioned against the inner surface 464 of the top wall 454d with the conductive holes 43 aligned with the grooves 465.

Figure 28:
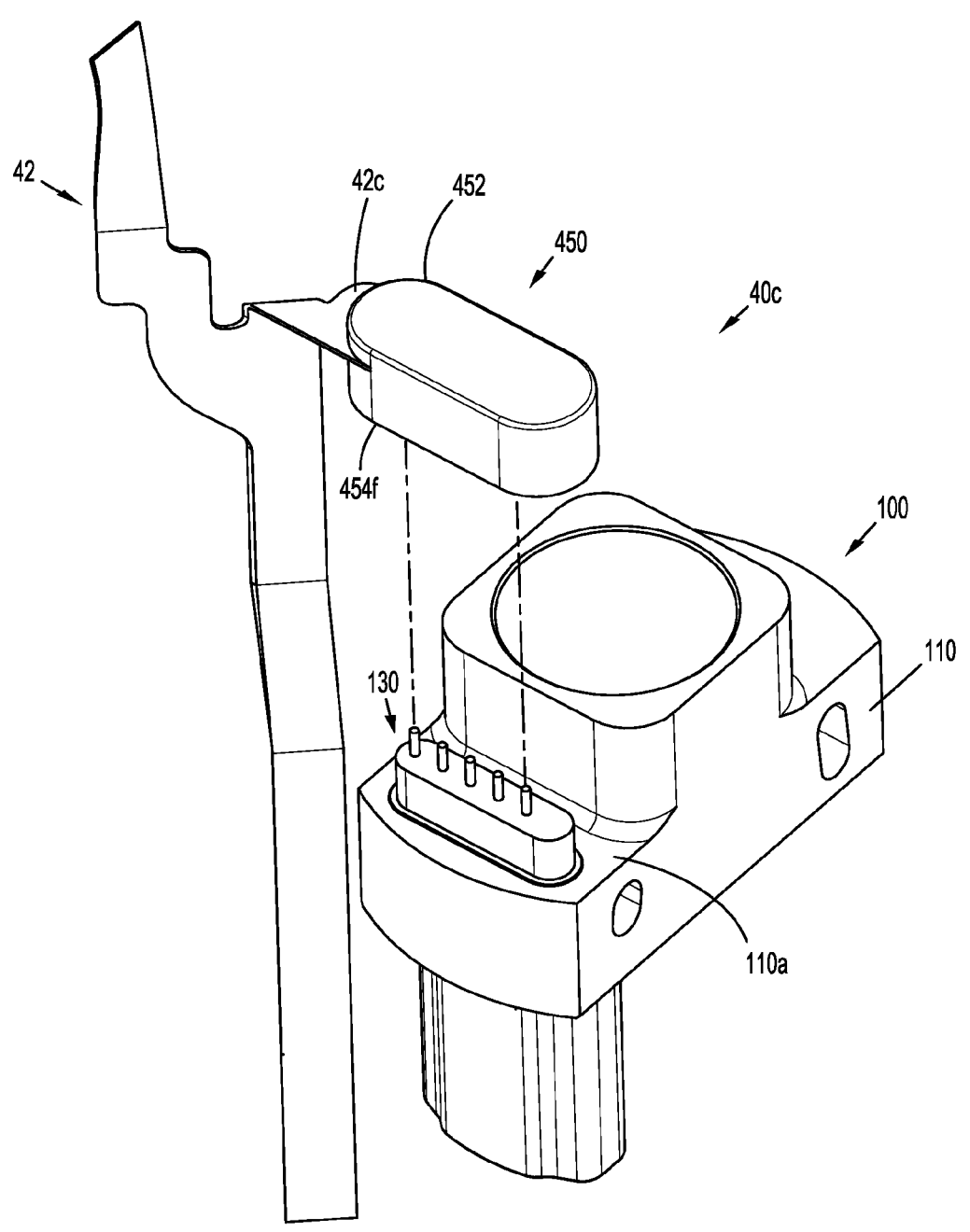
FIG. 28 is a perspective view of an electronic assembly in accordance with yet another aspect of the disclosure, the electronic assembly including a force sensor and a flex cable including an integrated housing of a seal assembly, shown with parts separated.
Figures 31, 32:
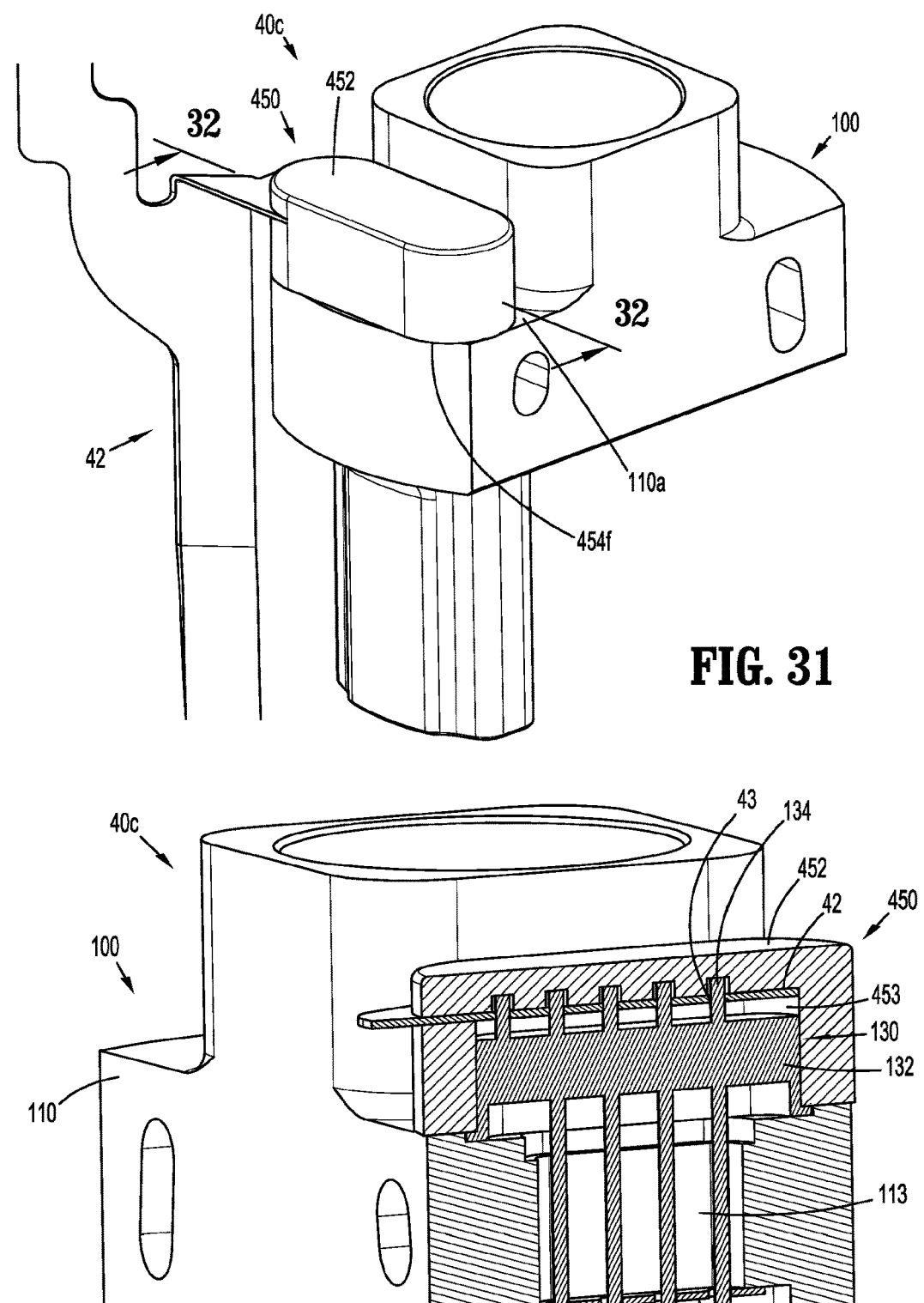
FIG. 31 is a perspective view of the electronic assembly of FIG. 28, shown in a fully assembled state.
FIG. 32 is a cross-sectional view of the electronic assembly of FIG. 31, taken along section line 32-32 of FIG. 31.

In a method of assembling the flex cable 42 and the seal assembly 450 onto the force sensor 100, as initially seen in FIG. 28, the third portion 42c of the flex cable 42 and the integrated housing 452 is aligned over the pin block assembly 130 with the bottom surface 454f of the housing 452 facing the proximal surface 110a of the substrate 110. As seen in FIG. 31, the housing 452 is then placed over the pin block assembly 130 (FIG. 28) such that the bottom surface 454f of the housing 452 contacts the proximal surface 110a of the substrate 110 and, as seen in FIG. 32, the pin block assembly 130 is disposed within the cavity 453 of the housing 452. During positioning of the flex cable 42 and housing 452 over the pin block assembly 130, the pins 134 of the pin block assembly 130 are received within the conductive holes 43 of the flex cable 42 and create an electronic connection therewith. Additionally, the fit of the housing 452 against the pin block assembly 130 and the proximal surface 110a of the substrate 110 forms a sealed perimeter around the pin block assembly 130 and the flex cable 42.

Figure 33:
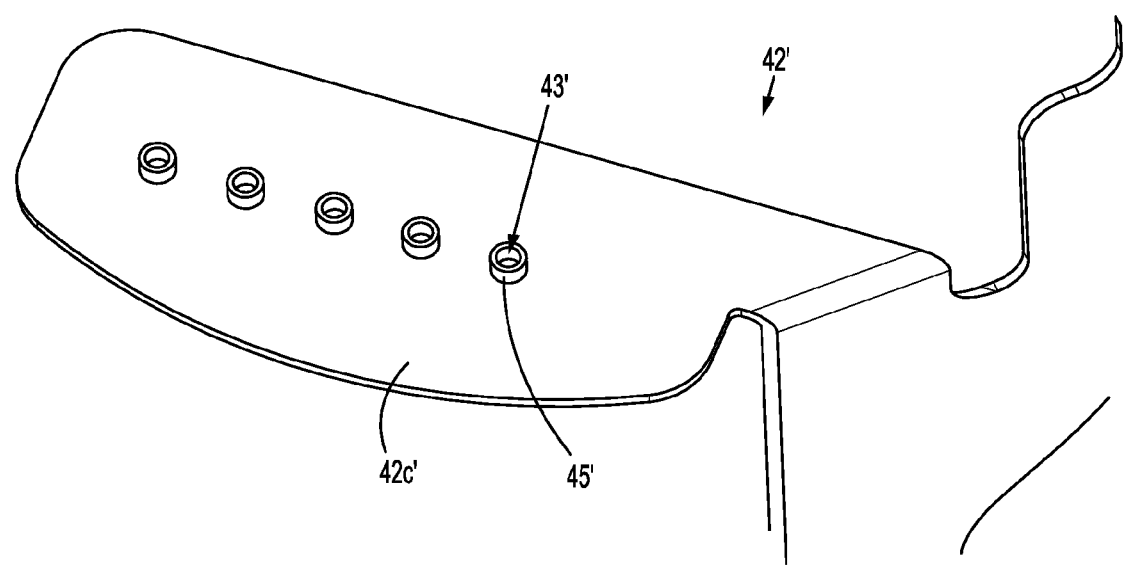
FIG. 33 is a perspective view of a flex cable in accordance with another aspect of the disclosure.

FIG. 33 illustrates a flex cable 42' in accordance with another aspect of the disclosure. The flex cable 42' is substantially similar to the flex cable 42 (FIG. 30) except that the flex cable 42' further includes a plurality of conductive receptacles 45' (referred to herein generally as conductive receptacles) extending around the conductive holes 43'. The conductive receptacles 45' extend proximally and distally beyond the surface of the third portion 42c' of the flex cable 42' thereby increasing the conductive surface area of the conductive holes 43'.

Figure 34:
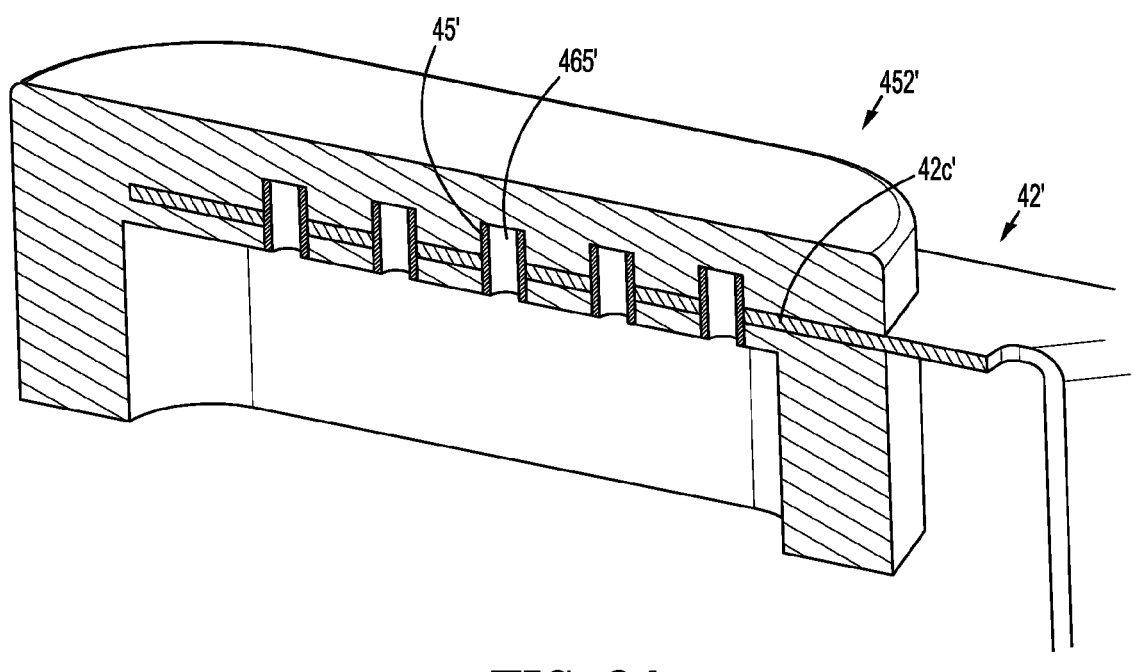
FIG. 34 is a cross-sectional view the flex cable of FIG. 33 including an integrated housing of a seal assembly in accordance with another aspect of the disclosure.

FIG. 34 illustrates a housing 452' in accordance with another aspect of the disclosure integrated onto the flex cable 42'. The housing 452' is substantially similar to the housing 452 (FIG. 30) except that the grooves 465' in the housing 452' are overmolded onto the receptacles 45' and the third portion 42c' of the flex cable 42' is disposed within the top wall 454d' of the housing 452'. When the flex cable 42' with integrated housing 452' is mated with the pin block assembly 130 (FIG. 32) an electrical connection is created between flex cable 42' and the pin block assembly 130 in combination with a mechanical seal of the housing 452' to the block body 132 (FIG. 32) of the pin block assembly 130.

Figure 35:
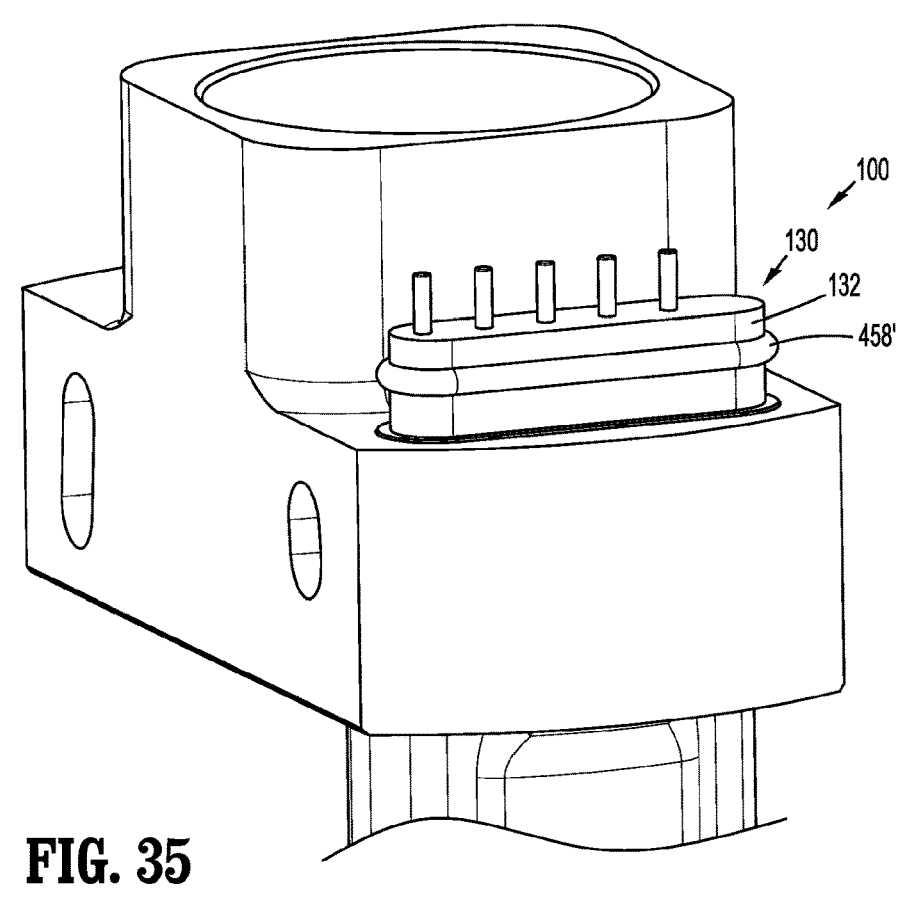
FIG. 35 is a perspective view of a force sensor including a gasket of a seal assembly in accordance with yet another aspect of the disclosure.
Figure 36:
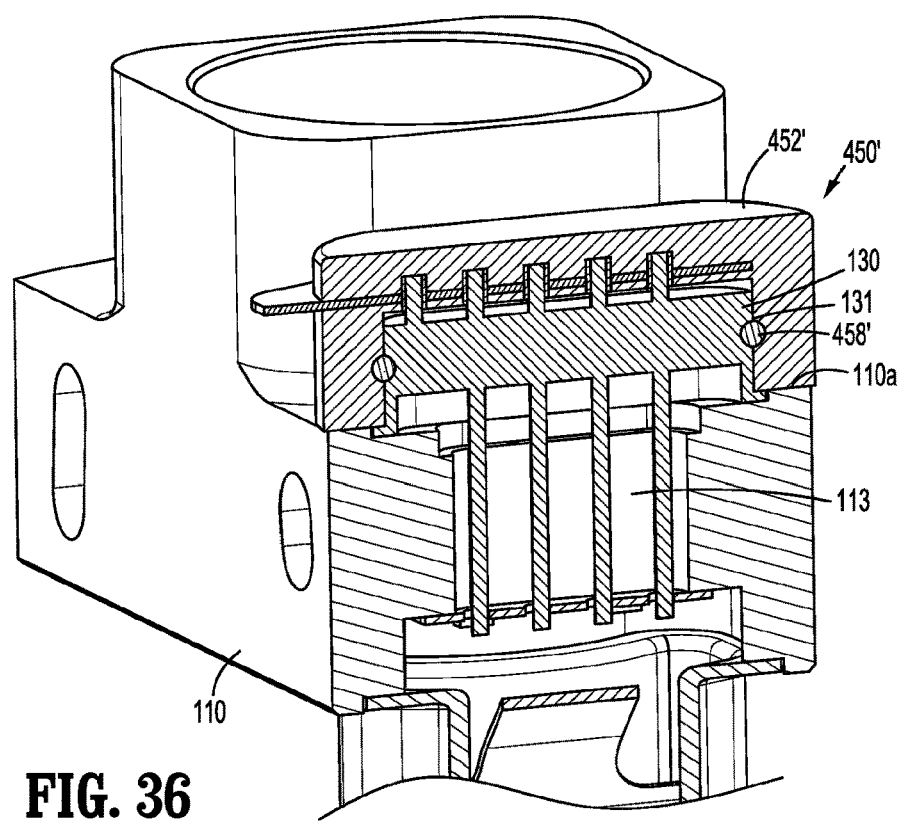
FIG. 36 is a cross-sectional view of an electronic assembly including the flex cable and integrated housing of FIG. 34 and the force sensor and gasket of FIG. 35, shown in a fully assembled state.

As shown in FIG. 35, to further enhance the seal between the housing 452, 452' (FIGS. 30 and 34) and the force sensor 100, a seal assembly 450' (FIG. 36) further includes a gasket 458' extending around the block body 130 of the pin block assembly 130 to enhance the interface and seal between the housing 452, 452' and the block body 130 as shown, for example, in FIG. 36. In some aspects, a groove 131 is defined around the block body 132 of the pin block assembly 130 for receipt of the gasket 458' therein to aid in retaining the gasket 458' against the block body 130 in spaced relation relative to the proximal surface 110a of the substrate 110. In other aspects, the gasket 458' may be positioned around the block body 130 and against the proximal surface 110a of the substrate 110 to enhance sealing of the pin block assembly 130 within the housing 452' as well as sealing of the opening in the cavity 113 of the substrate 110.

While illustrated as being used in a hand-held powered surgical device 1 hereinabove, it is contemplated, and within the scope of this disclosure for the seal assemblies to be configured for use with various electromechanical and/or electrosurgical instruments and systems. For example, the seal assemblies may be utilized in non-motor driven yet powered surgical devices (e.g., reusable surgical devices subject to washing and/or sterilization procedures). As another example, the seal assemblies may be utilized in robotic surgical systems. Further, while the end effector 20 of the surgical device 1 is shown as a stapler, it should be understood that the various electromechanical and/or electrosurgical instruments and systems may use end effectors having different configurations, e.g., graspers, dissectors, retractors, scissors, knives, forceps, clip appliers, cauterizers, aspirators, irrigators, etc.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of this disclosure, and that such modifications and variation are also included within the scope of this disclosure. Therefore, the above description should not be construed as limiting, but merely as exemplifications of aspects of the disclosure and the subject matter of this disclosure is not limited by what has been particularly shown and described. Thus, the scope of the disclosure should be determined by the appended claims and their legal equivalents, rather than by the examples given.

What is claimed is:

1. An electronic assembly comprising:
a first electronic component including a substrate and a first electrical connecting portion secured to the substrate;
a second electronic component including a second electrical connecting portion, the second electrical connecting portion connected to the first electrical connecting portion forming an electronic connection between the first and second electronic components; and
a seal assembly including:
a housing defining a cavity therein and having one or more open sides, the housing positioned over the electronic connection and mated by a gasket to the substrate resulting in a single open side; and
an encapsulate disposed within the cavity of the housing and covering the electronic connection, the encapsulate sealing closed the single open side of the housing.

2. The electronic assembly according to claim 1, wherein the first electronic component is a sensor.

3. The electronic assembly according to claim 1, wherein the second electronic component is a flexible electrical cable.

4. The electronic assembly according to claim 1, wherein the electronic connection is a solder connection.

5. The electronic assembly according to claim 1, wherein the one or more open sides of the housing of the seal assembly includes an open bottom and an open end, the housing positioned over the electronic connection with the open bottom positioned against the substrate of the first electronic component thereby closing the open bottom.

6. The electronic assembly according to claim 1, wherein the encapsulate is formed using a curable liquid resin.

7. The electronic assembly according to claim 1, wherein the housing is force mated to the substrate to form a seal between the housing and the substrate.

8. The electronic assembly according to claim 1, wherein the housing includes a rib disposed within the cavity forming an interference fit between the housing and the first electrical connecting portion of the first electronic component.

9. The electronic assembly according to claim 1, wherein the housing includes a living hinge.

10. The electronic assembly according to claim 1, wherein the encapsulate is only exposed outside of the housing at an interface of the encapsulate with the single open side of the housing.

11. The electronic assembly according to claim 1, wherein the second electronic component extends out of the seal assembly through the encapsulate closing the single open side of the housing.

12. A method of sealing an electronic connection between a first electronic component and a second electronic component, the method comprising:
positioning a housing of a seal assembly over an electronic connection formed between a first electrical connecting portion of a first electronic component and a second electrical connecting portion of a second electronic component, the housing defining a cavity therein and having one or more open sides, wherein positioning the housing over the electronic connection results in the housing having a single open side; and
filling the single open side of the housing with an encapsulate of the seal assembly to encapsulate the electronic connection and seal close the single open side of the housing.

13. The method according to claim 12, further comprising soldering the first and second electrical connecting portions together to form a solder connection.

14. The method according to claim 12, wherein the one or more open sides of the housing of the seal assembly includes an open bottom, and wherein positioning the housing over the electronic connection includes positioning the open bottom of the housing against a substrate of the first electronic component to close the open bottom.

15. The method according to claim 14, wherein the one or more open sides of the housing of the seal assembly includes an open end, and wherein positioning the housing over the electronic connection includes facing the open end of the housing towards the electronic connection and sliding the housing onto the substrate and over the electronic connection.

16. The method according to claim 12, further comprising curing the encapsulate after filling the housing with the encapsulate.

17. The method according to claim 12, further comprising force mating the housing to a substrate to form a seal between the housing and the substrate.

18. The method according to claim 12, wherein the second electronic component extends out of the seal assembly through the single open side of the housing, and wherein filling the single open side of the housing with the encapsulate includes pouring the encapsulate around a portion of the second electronic component extending through the single open side of the housing.

19. A surgical device comprising:
a handle assembly;
an adapter assembly extending from the handle assembly;
an end effector releasably secured to the adapter assembly; and
an electronic assembly disposed within the adapter assembly, the electronic assembly configured to enable communication between the handle assembly and the end effector, the electronic assembly including:
a first electronic component including a substrate and a first electrical connecting portion secured to the substrate;
a second electronic component including a second electrical connecting portion, the second electrical connecting portion connected to the first electrical connecting portion forming an electronic connection between the first and second electronic components; and
a seal assembly including:
a housing defining a cavity therein and having one or more open sides, the housing positioned over the electronic connection and mated to the substrate resulting in a single open side; and an encapsulate disposed within the cavity of the housing and covering the electronic connection, the encapsulate sealing closed the single open side of the housing;

wherein the housing includes a rib disposed within the cavity forming an interference fit between the housing and the first electrical connecting portion of the first electronic component.

* * * * *